(12) United States Patent
Xia

(10) Patent No.: US 12,274,849 B2
(45) Date of Patent: *Apr. 15, 2025

(54) INTRODUCTION NEEDLE AND TATTOO DEVICE

(71) Applicant: Tingting Xia, Jiangsu (CN)

(72) Inventor: Tingting Xia, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/650,158

(22) Filed: Apr. 30, 2024

(65) Prior Publication Data

US 2024/0277988 A1 Aug. 22, 2024

Related U.S. Application Data

(63) Continuation of application No. PCT/CN2024/083736, filed on Mar. 26, 2024, and a continuation of application No. PCT/CN2023/129076, filed on Nov. 1, 2023, and a continuation-in-part of application No. 18/243,091, filed on Sep. 6, 2023, now Pat. No. 11,998,713, which is a continuation of application No. PCT/CN2022/071556, filed on Jan. 12, 2022.

(30) Foreign Application Priority Data

| Apr. 14, 2021 | (CN) | .......................... 202110402463.0 |
| Nov. 2, 2022 | (CN) | .......................... 202211364289.6 |
| Mar. 28, 2023 | (CN) | .......................... 202320643645.1 |

(51) Int. Cl.
*A61M 37/00* (2006.01)

(52) U.S. Cl.
CPC .............................. *A61M 37/0084* (2013.01)

(58) Field of Classification Search
CPC .......... A61M 37/0076; A61M 37/0084; A61M 2202/0007; A61M 2205/106; A61M 2205/8281; A61M 2210/04; A61M 5/46
See application file for complete search history.

(56) References Cited

U.S. PATENT DOCUMENTS

| 7,695,486 | B2 * | 4/2010 | Dixon | ............... | A61M 37/0076 |
| | | | | | 606/186 |
| D888,240 | S * | 6/2020 | Parcon | .............. | A61M 37/0076 |
| | | | | | D24/146 |
| 11,998,713 | B2 * | 6/2024 | Xia | ................... | A61M 37/0076 |
| 11,998,714 | B2 * | 6/2024 | Xia | ................... | A61M 37/0084 |
| 2011/0009860 | A1 * | 1/2011 | Chornenky | ............ | A61B 18/14 |
| | | | | | 606/41 |
| 2019/0217072 | A1 | 7/2019 | Xiao | | |
| 2020/0330740 | A1 | 10/2020 | Bonnett | | |

* cited by examiner

*Primary Examiner* — Robert A Lynch

(57) ABSTRACT

An introduction needle includes a needle piercing portion. The needle piercing portion comprises a needle tooth and a substrate; the needle tooth is fixedly disposed on a portion of a first side surface of the substrate; and when the needle tooth pierces into the skin, the remaining portion of the first side surface of the substrate is configured to abut against an outer surface of the skin.

17 Claims, 51 Drawing Sheets

INTRODUCTION NEEDLE AND TATTOO DEVICE

CROSS REFERENCE TO RELATED APPLICATIONS

The present application is continuation-in-part application of the U.S. patent application Ser. No. 18/243,091, filed on Sep. 6, 2023. The present application is continuation of: the international patent application No. PCT/CN2023/129076, which was filed on Nov. 1, 2023, and claims priority of Chinese patent application No. 202211364289.6, filed on Nov. 2, 2022; and the international patent application No. PCT/CN2024/083736, which was filed on Mar. 26, 2024, and claims priority of Chinese patent application No. 202320643645.1, filed on Mar. 28, 2023. The contents of which are incorporated herein by their entireties.

TECHNICAL FIELD

The present disclosure relates to the field of tattoo tools, and in particular to an introduction needle and a tattoo device.

BACKGROUND

Tattoo is a method of embellish a face by introducing a colour pigment into a certain depth of the skin, and the colour pigment may be retained for months to years. A working principle of tattoo is disrupting the skin and applying color to the skin. An essential component of a tattoo tool in the art is a metal needle filament having one sharpened end. As demands of users are changed, semi-permanent tattoo has emerged in the art. For the semi-permanent tattoo, based on the principle of disrupting the skin and applying color to the skin, the pigment is retained at a shallower layer of the skin, i.e., at a layer between the epidermis and the dermis, or at a layer of the dermis near the epidermis. For a tattoo obtained in this way, the colour may be retained for 1-2 years and may be metabolized naturally.

Tattoo is actually coloring the skin by minimal invasion. The pigment is planted in the skin tissue to form a stable colour block. Since the epidermis is quite thin and is semi-translucent, the color of the pigment can be observed through the epidermis layer to cover up defects, to express the beauty but avoid shortcomings, and to modify and embellish the skin. Any pigment that is introduced into the skin is in a form of a small particle, and a diameter of the small particle is less than one micrometer. The small particle may be quickly surrounded by collagen but cannot be phagocytosed by phagocytes, and therefore, a mark is formed on the skin.

While producing a tattoo, a tattooist needs to use a tattoo tool to leave a mark on the skin. In order to produce the tattoo, which may be retained in the skin for 1 to 2 year and metabolized naturally afterwards, the tattooist needs to accurately control, while producing the tattoo, a depth that the needle reaches in the skin, and that is, a length that a needle projects out of the tattoo tool must be accurately adjusted. However, in the art, the tattoo tool cannot accurately control a length that the metal needle filament at a front end of the tattoo tool projects out of the tattoo tool and the depth that the needle reaches in the skin. The tattooist has to adjust, by naked eyes and based on experience, the length that the metal needle filament at the front end of the tattoo tool projects out of the tattoo tool. While the tattoo tool is started up for adjustment, the tattooist has to adjust, by naked eyes, the length that the metal needle filament projects out of the tattoo tool while the needle filament is extending and retracting at a high speed. The adjustment, performed based on experience, may have a large error rate, it may be difficult for learners to learn the method, and the tattoo method may not be easily industrialized.

Therefore, it is urgent to propose a technical solution to solve the problems in the art.

SUMMARY OF THE DISCLOSURE

The present disclosure provides an introduction needle including a needle piercing portion. The needle piercing portion comprises a needle tooth and a substrate; the needle tooth is fixedly disposed on a portion of a first side surface of the substrate; and when the needle tooth pierces into the skin, the remaining portion of the first side surface of the substrate is configured to abut against an outer surface of the skin.

The present disclosure further provides a tattoo device, including the introduction needle in the above and a driving mechanism. The driving mechanism is configured to drive the liquid guiding member to move reciprocately to drive the needle piercing portion to inject into the skin and leave out of the skin repeatedly.

BRIEF DESCRIPTION OF THE DRAWINGS

In order to more clearly illustrate the technical solutions in the embodiments of the present disclosure or in the art, the accompanying drawings for the description of the embodiments or the art will be briefly introduced below. Obviously, the accompanying drawings in the following description are only some of the embodiments of the present disclosure. Any ordinary skilled person in the art may obtain other drawings based on the accompanying drawings without creative work.

DETAILED DESCRIPTION

Figure 1A:
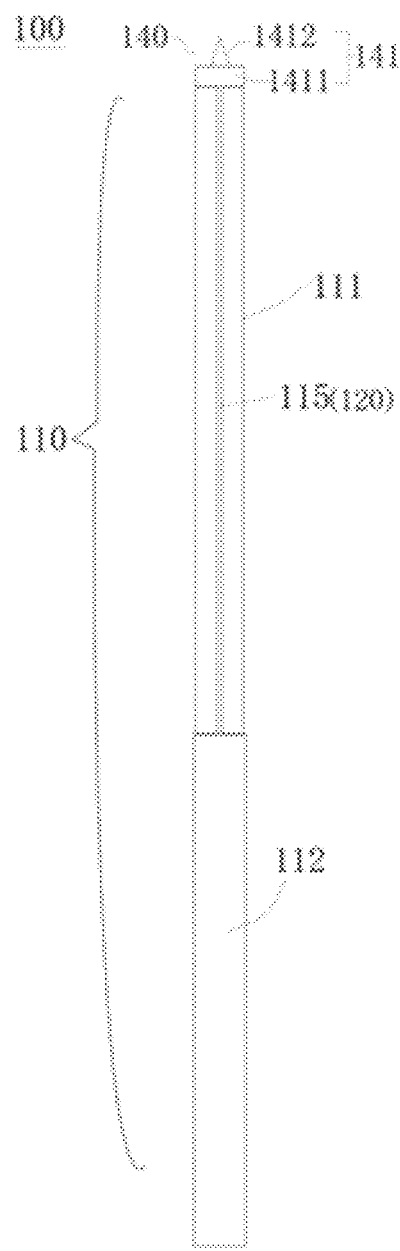
FIG. 1(a) is a structural schematic view of an introduction needle according to an embodiment of the present disclosure.
Figure 1B:
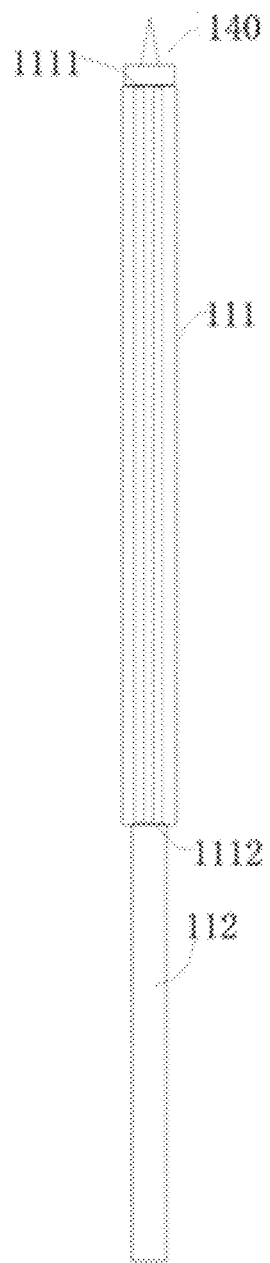
FIG. 1(b) is another structural schematic view of an introduction needle according to an embodiment of the present disclosure.
Figure 1C:
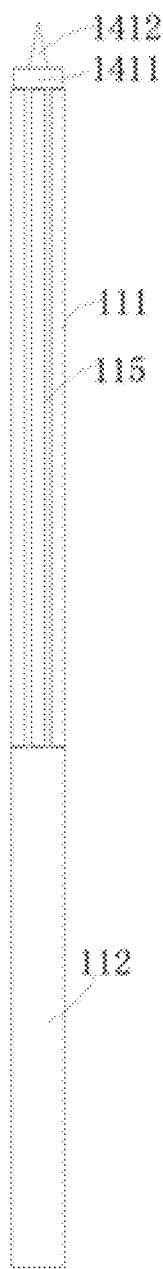
FIG. 1(c) is another structural schematic view of an introduction needle according to an embodiment of the present disclosure.

The technical solutions of the embodiments of the present disclosure will be described clearly and completely in the following by referring to the accompanying drawings. Obviously, the described embodiments show only a part of but not all of the embodiments of the present disclosure. All other embodiments obtained, based on the embodiments of the present disclosure, by any ordinary skilled person in the art without making creative work shall fall within the scope of the present disclosure.

In the description of the present disclosure, it is to be understood that any orientation or positional relationship indicated by the terms "top", "bottom", "top", "bottom", "inside", "outside", and so on, is an orientation or a positional relationship as shown in the accompanying drawings. The terms are used only to facilitate and simplify the description of the present disclosure, but do not indicate or imply that the device or element referred to must have a particular orientation or must be constructed and operated in a particular orientation. Therefore, the terms cannot be interpreted as limiting the present disclosure. In the present disclosure, the term "a plurality of" means two or more, unless otherwise expressly and specifically limited.

In the present disclosure, unless otherwise expressly provided and limited, the terms "mounted", "connected", "coupled", "fixed", and so on, shall be understood in a broad sense. For example, connection may be fixed connection, detachable connection, or two elements being configured as a one-piece structure; or may be mechanical connection or electrical connection; or may be direct connection, indirect connection through an intermediate medium, or two elements being internally connected or being interactive with each other. Any ordinary skilled person in the art shall understand specific meanings of the above terms in the present disclosure in a case-by-case manner.

The present disclosure will be illustrated in the following by referring to the drawings and the embodiments.

Figure 22A:
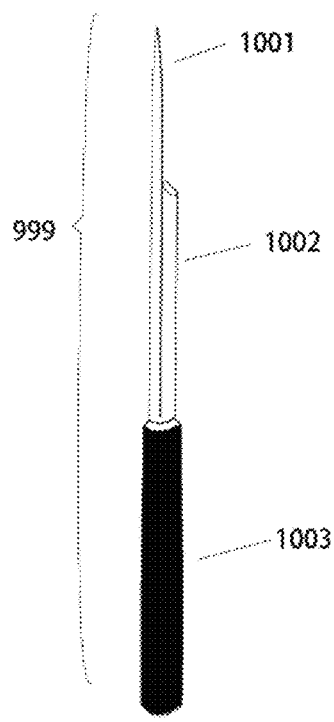
FIG. 22(a) is a structural schematic view of a single needle device.
Figure 22B:
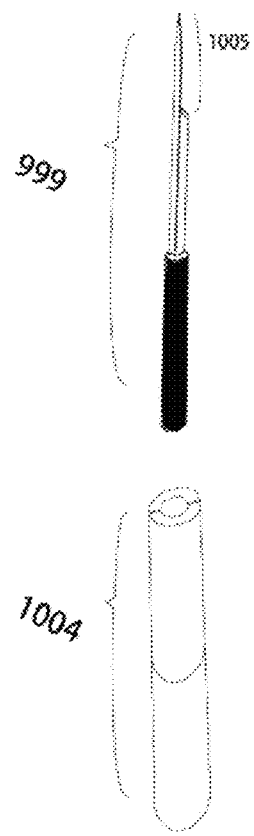
FIG. 22(b) is a schematic view of the single needle device shown in FIG. 22(a) being separated from a tattoo rod.

In order to perform fine colouring on a small area on the skin, for a tattoo device in the art, a single metal needle filament has a sharpened tip, serving as an operating end, and the single needle filament is welded to a needle handle. Further, the needle handle is secured, through a fixation end of the needle handle, to a tattoo rod. In this way, a single needle device is formed. As shown in FIG. 22(a), FIG. 22(a) shows a structural schematic view of the single needle device. The single needle device 999 includes a metal needle filament 1001, a needle handle 1002, a fixation end 1003 of the needle handle, a tattoo rod 1004, and a needle tip portion 1005. The single needle device 999 of FIG. 22(a) includes the single metal needle filament 1001 having a sharpened end, the needle handle 1002, the fixation end 1003 of the needle handle, the tattoo rod 1004, and the needle tip portion 1005. The needle tip portion 1005 is a part of the sharpened end of the single metal needle filament and protrudes from the needle handle. A length of the needle tip of the single needle device in the art is in a range from 3 mm to 10 mm. The needle tip 1005 of the single needle device 999 in the present embodiment is 3 mm. FIG. 22(b) is a schematic view of the single needle device shown in FIG. 22(a) being separated from a tattoo rod.

In an embodiment, the above single needle device may be taken to perform point-pricking to colour the skin. The point-pricking refers to the device repetitively pricking single points of the skin to bring the pigment into the skin. Alternatively, the above single needle device may be taken to draw lines to the colour the skin. Drawing lines to the colour the skin refers to the device breaking the skin from a single point and subsequently streaking the skin to bring the pigment into the skin. Although a process of manufacturing the single needle device in the art may be simple and the single needle device may be easily produced, the operating end of the single needle device in the art may cause the following colouring and safety problems. While colouring the skin to produce the tattoo, the operating end may prick the skin to reach an excessively large depth, and in this case, the pigments may spread outside a target colour area under the skin. Therefore, the pigment may be unable to be completely metabolized for several years, also known as "colour fading" in the tattoo industry.

According to scientific data, an average thickness of the epidermis of the human face is in a range from 0.2 mm to 1.0 mm, an average thickness of the epidermis at the eyebrow region is 0.5 mm, and an average thickness of the epidermis at the eyelid region is 0.33 mm. A thickness of one piece of conventional A4 paper of 80 g is 0.11 mm. That is, a thickness of the epidermis at the relatively thinner region of the human face is approximately equal to thicknesses of 2 to 3 pieces of conventional A4 paper. It may be difficult to control, based on subjective experience, a depth that is reached by the single needle device in the art piercing into the skin having the above thickness. By analyzing a large number of cases, "colour fading" cases may occur highly frequently, and this is because a piercing depth of the single needle device of the tattoo tool in the art may not be limited effectively, and a large error may be resulted due to the piercing depth being controlled by subjective determination of the operator only. Therefore, the piercing depth of tattoo may be determined and controlled in advance according to the thickness of the epidermis of various operating regions, such that a bleeding rate may be reduced to prevent occurrence of "colour fading".

According to accumulated data from the industry and experimental analysis, when the skin at the eyebrow region is pierced for a depth of 0.05 mm to 1.0 mm, the pigment may be retained at the skin for 3 months to 10 years in average. As the skin is pierced more deeply, the pigment may be retained longer. When the piercing depth is more than 1.0 mm, an average time length that the colour can be retained is more than 10 years. In the art, semi-permanent tattoo is the main demand in the market. The semi-permanent tattoo refers to the colour being retained for 1-2 years, and the piercing depth into the skin shall be controlled in the range of 0.3 mm to 0.6 mm, i.e., approximately thicknesses of 2-4 pieces of conventional A4 paper, each in the weight of 80 g.

In order to verify a relationship between the depth that the single needle device pierces into the skin and the time length that the colour is retained, a following verification experiment is performed.

For the tattoo tool in the art, a single needle device in a commonly used model (i.e., a diameter of the needle filament is 0.30 mm, a length of the needle tip is 3 mm) is taken to perform various pricking tests. For each of the various pricking tests, the single needle device is taken to prick a simulated silicone skin, and all simulated silicone skins applied in the various pricking tests are in a same specification. For the various pricking tests, an average height that the needle tip leaves the simulated silicone skin is 5 mm, and the needle tip pricks the simulated silicone skin twice per second in average. When an average depth that the needle tip pierces into the simulated silicone skin is 0.7 mm, approximately 0.06 kg force is applied to achieve the average depth. When an average depth that the needle tip pierces into the simulated silicone skin is 0.3 mm, approximately 0.04 kg force is applied to achieve the average depth. That is, that is, a difference of 0.02 kg force causes a 0.4 mm error in the depth that the needle tip pierces into the simulated silicone skin. The difference of 0.02 kg force is equivalent to a weight of 4-5 pieces of conventional A4 paper. It may be difficult to achieve this precision subjectively by human experience. For example, at the eyebrow region, when the depth that the skin is pierced is in a range of 0.3 mm to 0.6 mm, the colour may be retained to for 1-2 years. The error of only 0.02 kg force may cause the needle tip to pierce into the skin excessively deeply, resulting in the colour being retained for an excessively long period of time. Therefore, the main demand of retaining the colour in the skin for 1-2 years may not be met, customer complaints may be caused easily.

Therefore, the depth that the single needle device of the tattoo tool in the art pierces into the skin cannot be precisely controlled, causing the "colour fading" problems. Further, the depth that the single needle device pierces into the skin is closely related to the time length that the pigment is retained in the skin. An effect of the tattoo may be affected since depths of various piercings are inconsistent and not controllable.

In order to solve deficiencies of the single needle device in the art, the present disclosure provides a tattoo needle, wherein the depth that the tattoo needle may pierce into the skin may be accurately defined in advance, such that the tattoo needle may be prevented from piercing into the skin excessively deeply, and therefore, the pigments may be prevented from spreading to a non-target colouring region.

A specific structure of the introduction needle provided by the present disclosure will be described in detail below by referring to the accompanying drawings.

Embodiment 1

As shown in FIG. 1(*a*) to FIG. 1(*d*), in an embodiment, an introduction needle 100 may include a liquid guiding member 110 and a needle piercing portion 140 disposed at an end of the liquid guiding member 110. The needle piercing portion 140 includes a piercing projection 141. The piercing projection 141 includes a substrate 1411 and a needle tooth 1412. The needle tooth 1412 is fixedly arranged on an end face of the substrate 1411. A central axis of the needle tooth 1412 is perpendicular to the end face of the substrate 1411. When the needle is piercing the skin, the substrate 1411 may limit a depth that the needle pierces the skin. The substrate 1411 presses against the skin to limit the depth that the needle tooth 1412 pierces into the skin. The liquid guiding member 110 may be columnar. The other end face of the substrate 1411 is fixed to an end of the columnar liquid guiding member 110. A central axis of the columnar liquid guiding member 110 is parallel to the central axis of the needle tooth 1412. The structure of the introduction needle 100 may be similar to a pen. The liquid guiding member 110 may be similar to a barrel of the pen. The needle piercing portion 140 may be similar to a tip of the pen. The liquid guiding member 110 may pierce the skin in the vertical direction, ensuring that a piercing position may not be shifted, the needle tip may not slip, and a redundant wound may not be generated.

As shown in FIG. 1(*a*) to FIG. 1(*d*), in an embodiment, the liquid guiding member 110 may include a liquid guiding post 111 and a connecting rod 112 connected to the liquid guiding post 111. That is, the liquid guiding member 110 includes two parts, one of the two parts guides ink to flow, and the other one of the two parts is configured for connection and driving. The connecting rod 112 is connected to a drive portion. The liquid guiding member 110 reciprocates, driven by the drive portion, along the central axis of the liquid guiding member 110. In a case, the drive portion may be a motorized rod, and that is, the connecting rod 112 of the liquid guiding member 110 is directly connected to the motorized rod (which may be fixed connection or a non-fixed connection (including abutting connection, hanging connection, and contact connection)). The motorized rod directly drives the liquid guiding member 110 to move. In another case, the drive portion may be an elastic member 170, such as a spring. The connecting rod 112 of the liquid guiding member 110 is connected to an end of the spring. A case (or a member fixedly connected to the case) is connected to the other end of the spring. Further, an external force is applied to drive the spring to be deformed. When the liquid guiding member 110 is moving along an axial direction of the case 150 towards a needle outlet end, the liquid guiding member 110 may be reset by a force from the deformed elastic member, such that the liquid guiding member 110 moves reciprocately within the case 150. In still another case, an operator may also hold the connecting rod 112 by hand to directly tattoo.

Figure 3A:
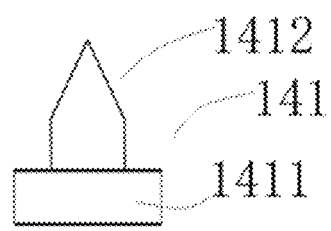
FIG. 3(a) is a front view of the piercing projection according to an embodiment of the present disclosure.
Figure 3B:
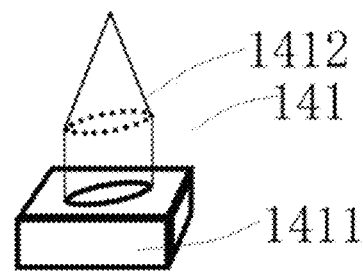
FIG. 3(b) is a perspective view of the piercing projection shown in FIG. 3(a).
Figure 3C:
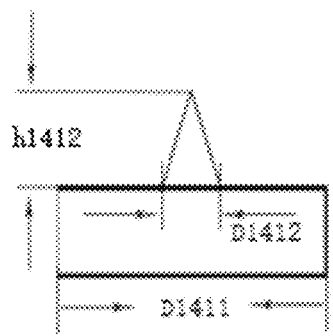
FIG. 3(c) is a front view of the piercing projection according to another embodiment of the present disclosure.
Figure 3D:
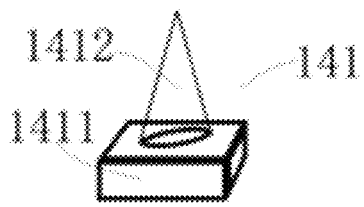
FIG. 3(d) is a perspective view of the piercing projection shown in FIG. 3(c).

In order to achieve various tattoo patterns and tattoo positions, the present embodiment provides a piercing projection 141, as shown in FIG. 3(d). The piercing projection 141 may include a substrate 1411 and a needle tooth 1412 arranged on the substrate 1411. The substrate 1411 serves as a depth limiting plate to limit a depth that the needle tooth 1412 pierces into the skin. The substrate 1411 and the needle tooth 1412 may be configured as a one-piece and integral structure, or configured as separated elements being fixedly connected with each other. When the substrate 1411 and the needle tooth 1412 are configured as the one-piece and integral structure, connection strength and stability of the needle tooth 1412 may be enhanced. Further, safety of the needle tooth 1412 may be improved while the needle tooth 1412 is piercing the skin. The one-piece and integral structure may be suitable for a high frequency piercing process.

The advantages of the introduction needle in the present disclosure, compared to the single needle device in the art, will be illustrated below by referring to FIGS. 23(a), 23(b), 24(a), and 24(b).

Figure 23A:
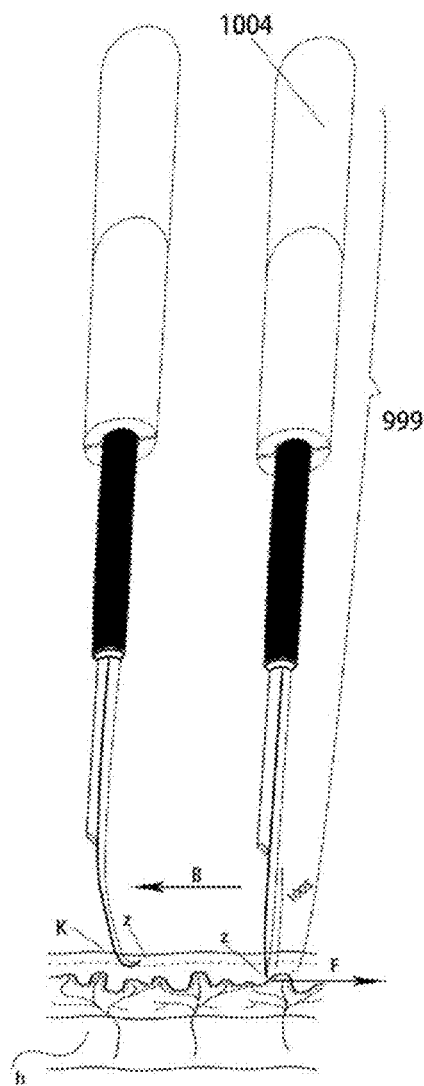
FIG. 23(a) is a cross-sectional of piercing a single needle device in the art into the skin.
Figure 23B:
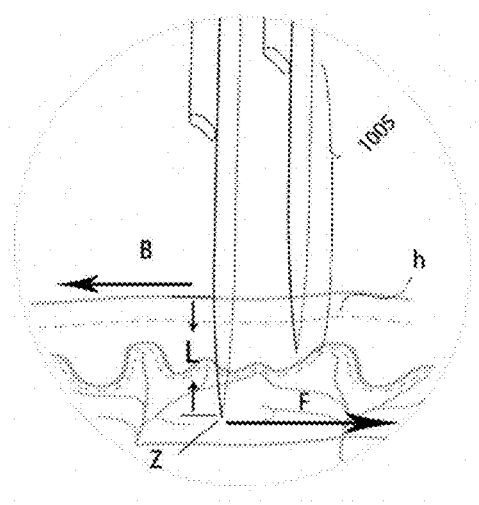
FIG. 23(b) is a schematic view of a force applied to a tip of the metal needle filament of the single needle device in the art, as shown in FIG. 34(a), while the single needle device is piercing into the skin.

As shown in FIG. 23(a), a cross-sectional structure of the skin is noted as h. The single needle device 999 of the tattoo tool in the art is connected to the tattoo rod 1004. The operator may hold the tattoo rod 1004 by hand to repetitively streak the skin along a direction indicated by an arrow B to colour the skin. A front end Z of the needle tip 1005 is under the skin and may be subjected to a resistance force F in a direction opposite to the direction B. The front end Z of the needle tip 1005 may be bent, as shown at K. Further, as shown in FIG. 23(b), the front end Z of the needle tip 1005 under the skin may be bent because of a force moment. The force moment=force arm*force (M=L*F). In a case that all forces in the horizontal direction are the same, as the needle tip pierces into the skin more deeply, the force arm L is larger, and the force moment M applied to the front end Z of the needle tip 1005 is larger. Therefore, the front end Z of the needle tip 1005 may be bent more easily. Therefore, the introduction needle provided by the present disclosure may limit the depth that the needle tip pierces into the skin, and that is, a maximum moment applied to the needle tip is limited, and the needle tip may be prevented from being bent.

Figure 24A:
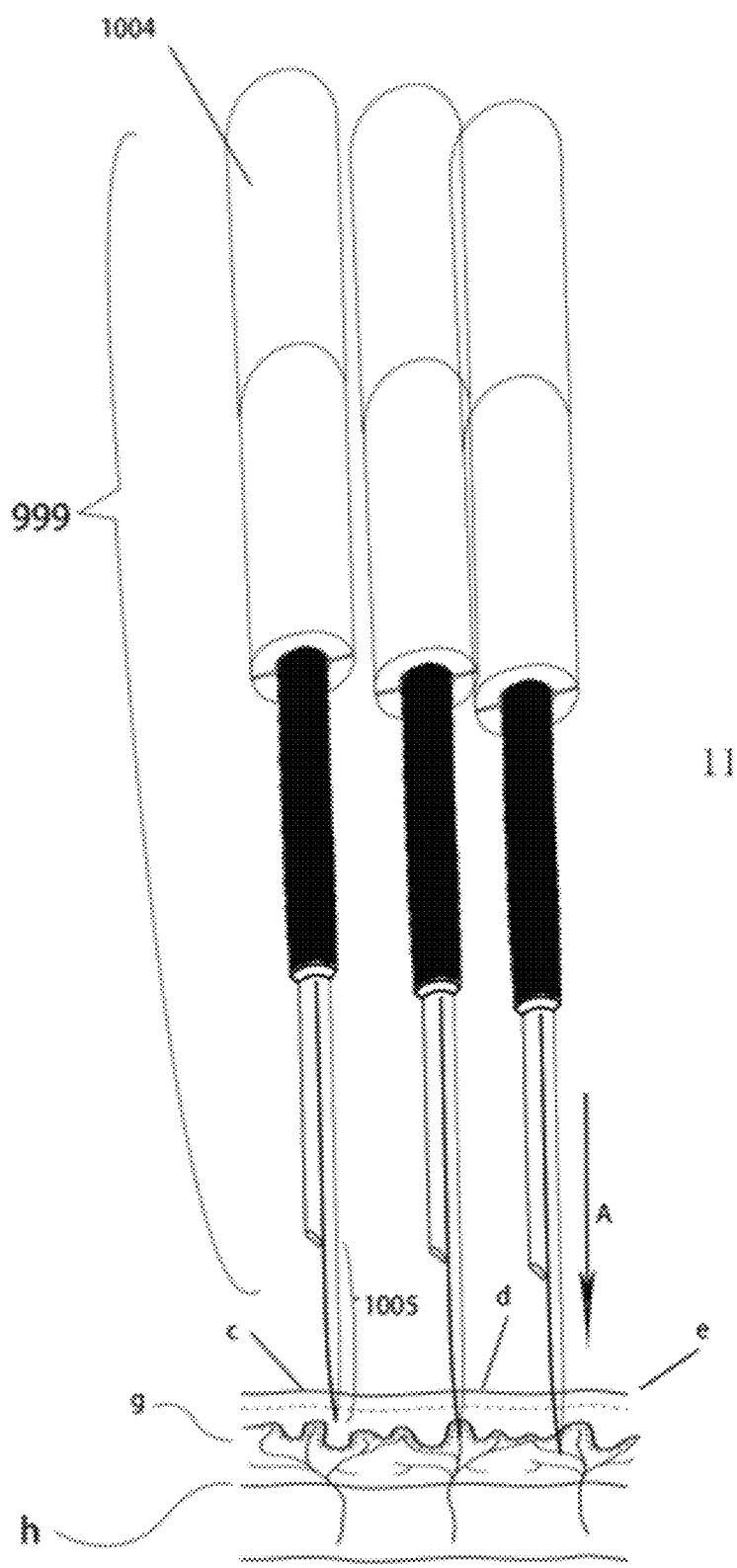
FIG. 24(a) is a cross-sectional view of the single needle device in the art piercing into the skin.
Figure 24B:
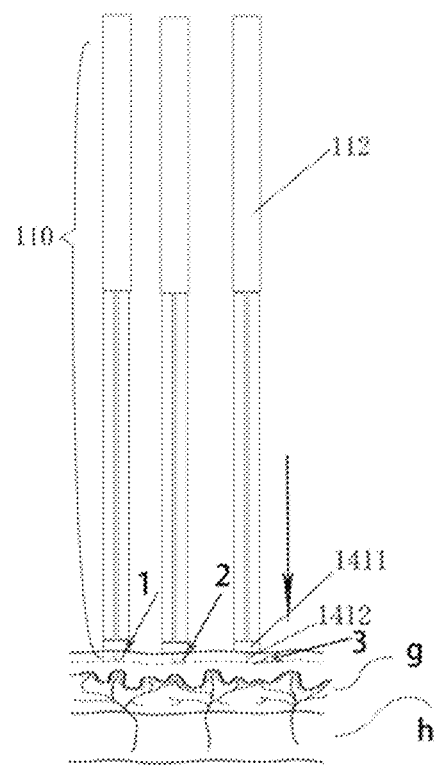
FIG. 24(b) is a cross-sectional view of the single needle device, according to an embodiment of the present disclosure, piercing into the skin.

As shown in FIG. 24(a), the cross-sectional structure of the skin is noted as h, and subcutaneous blood vessels are noted as g. The operator holds the tattoo rod 1004 by hand to repeatedly prick the skin along the arrow A in an up-down direction to colour the skin. The needle tip 1005 pierces into the skin to reach position as indicated by c, d, and e, in FIG. 24(a), and the position c, d, and e refer to different depths under the skin. The depths of the positions d and e show that the needle tip has reached locations at which the subcutaneous blood vessels are located. As shown in FIG. 24(b), the operator may alternatively directly hold the connecting rod 112 to repeatedly prick the skin to colour the skin. The needle tooth 1412 having a predetermined piercing length pierces into the skin, and the substrate 1411 contacts the skin to form a barrier, such that the piercing depth is limited. As indicated by points 1, 2, and 3 shown in FIG. 24(b), the piercing depths are controllable and are consistent. A height of the needle tooth 1412 is predetermined within a certain range to prevent the subcutaneous blood vessels from being pierced and to prevent the tip from being bent due to an excessive large force moment.

Embodiment 2

As shown in FIG. 3(c) to FIG. 3(d), in an embodiment, the needle tooth 1412 of the present disclosure may be a protrusion protruding from the substrate 1411. A size of a cross sectional area of the protrusion decreases along a direction that the needle teeth piece into the skin. For example, the size of the cross sectional area of the protrusion decreases in a direction from the substrate 1411 towards a free end of the protrusion. A bottom of the needle tooth is connected to the substrate 1411, and the free end of the needle tooth is a top end. Based on repeated experiments, in order to achieve a better effect of guiding the pigments, a height range $h1412$ of the needle tooth is 50 $\mu m \leq h1412 \leq 1000$ $\mu m$, and a diameter range $D1412$ of the bottom of the needle teeth is 20 $\mu m \leq D1412 \leq 500$ $\mu m$, in general, $D1412 \leq h1412$.

In an embodiment, the substrate 1411 is in an arbitrary polygonal shape. The needle tooth 1412 is disposed on an end face of the substrate 1411. In order to achieve the better effect of guiding the pigments, a minimum edge length of the substrate 1411 is recorded as $D1411$. In the case $D1411 > D1412$, the pigments may flow to reach the substrate 1411 from the relatively thick liquid guiding post 111 and may further be guided from the substrate to the needle tooth 1412.

Figure 4A:
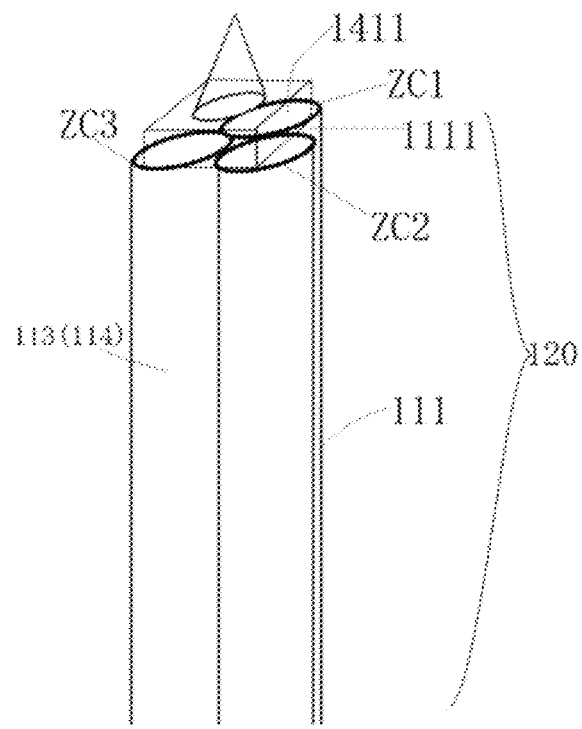
FIG. 4(a) is a perspective view of a portion of the introduction needle according to an embodiment of the present disclosure.
Figure 4B:
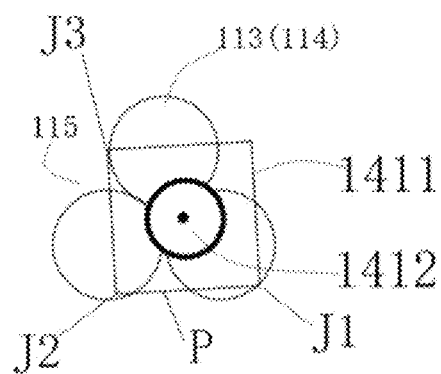
FIG. 4(b) is a schematic view of the introduction needle shown in FIG. 4(a), viewed from a viewing angle.
Figure 4C:
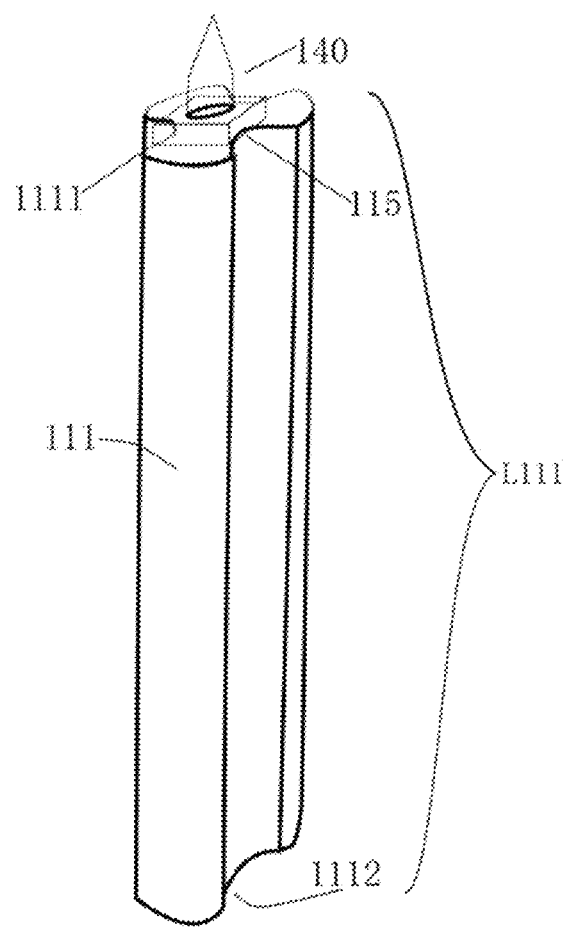
FIG. 4(c) is a perspective view of a portion of the introduction needle according to another embodiment of the present disclosure.
Figure 4D:
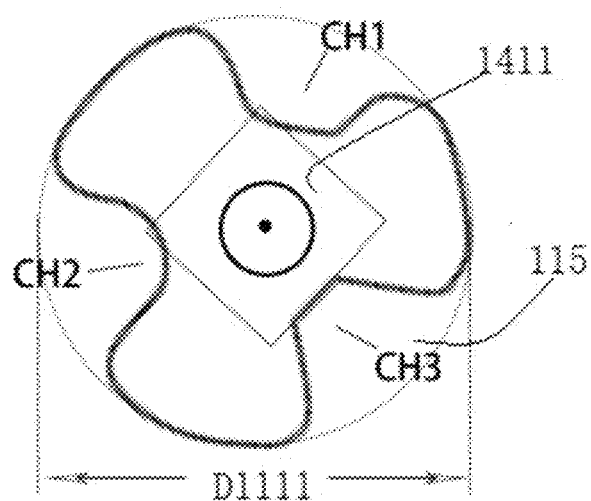
FIG. 4(d) is a schematic view of the introduction needle shown in FIG. 4(c), viewed from a viewing angle.

As shown in FIG. 4(d), a diameter of a first end face 1111 of the liquid guiding post 111 is $D1111$. Based on repeated experiments, in order to achieve the better effect of guiding the pigments and to have a certain extent of rigidity, 180 $\mu m \leq D1111 \leq 1800$ $\mu m$, and $D1111 > D1411$. Further as shown in FIG. 4(c) and FIG. 4(d), three channels 115 are defined in the liquid guiding post 111 (CH1, CH2, and CH3 in FIG. 4(c) each represents one of the three channels). As shown in FIG. 4(c), a length of the liquid guiding post 111 is $L111$, and $L111 > D1111$. In an embodiment, in order to allow the device to carry an increased amount of ink and to release the ink continuously and slowly, $L111 > 2 \times D1111$. That is, the length of the liquid guiding post 111 is greater than two times of the diameter of the first end face of the liquid guiding post 111. Of course, a cross section of the piercing projection 141, taken by the substrate 1411, may be arbitrary polygonal, for example, the cross section may be triangular, quadrilateral, pentagonal, or in other regular or irregular polygonal shapes. When the shape of the substrate 1411 is arbitrary polygonal, an axial length of the liquid guiding post 111 is at least two times of the length of the shortest edge of the first end face 1111 of the liquid guiding post 111, and the axial length of the liquid guiding post 111 is greater than a length of the longest edge of the first end face 1111.

Figure 5A:
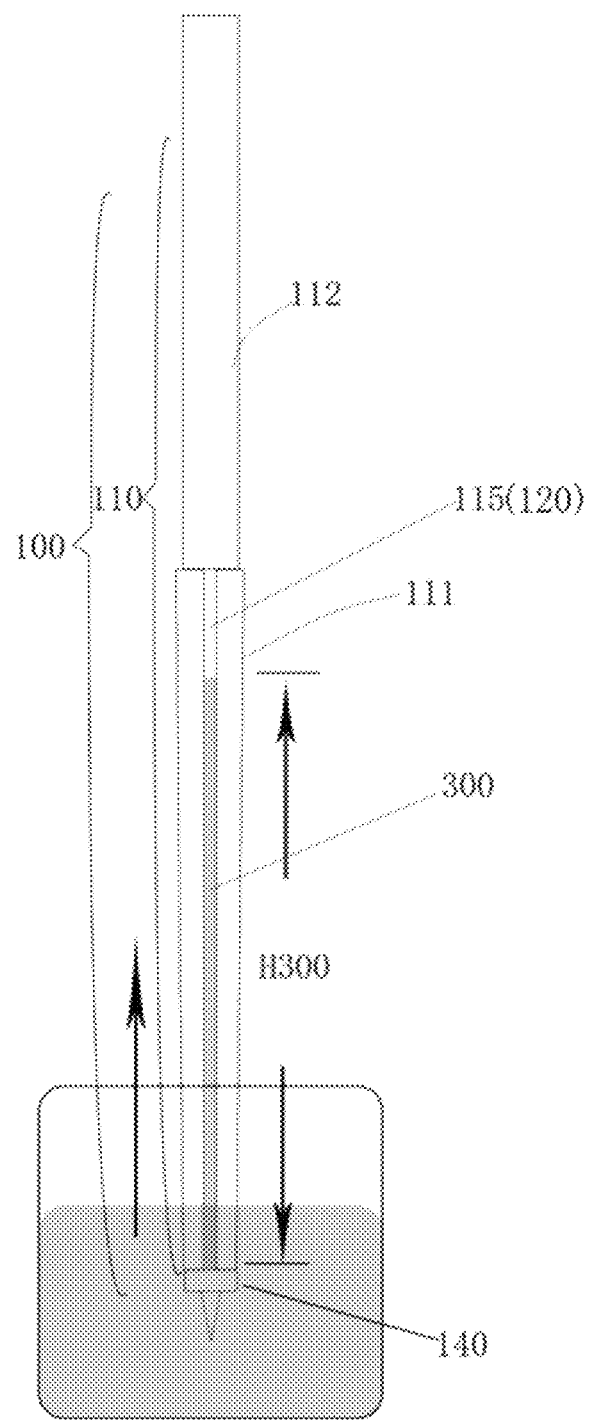
FIG. 5(a) is a schematic view showing a state of the introduction needle while the introduction needle is intaking ink, according to an embodiment of the present disclosure.

As shown in FIG. 5(a), the liquid guiding member 110 is arranged with a capillary liquid storage unit 120. A channel 115 in the capillary liquid storage unit 120 is defined in an outer wall of the liquid guiding member 110. Further, a capillary principle is applied to enable the channel 115 to store the pigments (the pigments and the ink in the present disclosure both refer to dyes that can colour the skin). The needle piercing portion 140 of the introduction needle 100 and a bottom of the channel 115 are submerged into the pigments, and the pigments rises along the channel 115 against the gravity. In this case, the channel 115 serves as a capillary liquid storage unit 120 that can temporarily store the pigments. When the introduction needle that has adsorbed the pigments is being used, the capillary liquid storage unit may continuously supply ink to the needle tooth of the needle piercing portion. When the liquid guiding member 110 is dipped into the pigments to intake the pigments, the pigments rises along the capillary liquid storage unit 120 to form a pigment column. For simple illustration, a height of the pigment column is recorded as H300.

Figure 5B:
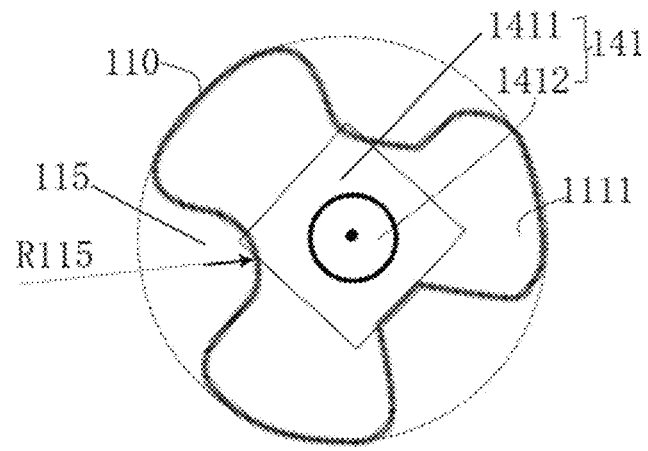
FIG. 5(b) is a top view of the introduction needle shown in FIG. 5(a), viewed from a viewing angle.

As shown in FIG. 5(b), the piercing projection 141 is fixed to the first end face 1111 of the liquid guiding member 110, and a radius of the channel 115 in the outer wall of the liquid guiding member 110 may be recorded as R115.

By collecting and analyzing data, a density of the pigments in the art at room temperature is about 0.7-1.31 g/ml, and a surface tension of the pigments at the room temperature is almost equal to a surface tension of water, which is about 72 mN/m. A capillary formula is as follows: a height h that the liquid rises along a capillary tube=2*surface tension coefficient*cos θ/(density of the liquid*gravitational acceleration g*radius of the capillary tube r). The θ is an angle between a liquid surface and a wall of the capillary tube. The radius of the channel R115 of the liquid storage unit 120 corresponds to the radius of the capillary tube r in the capillary formula. According to the experimental test and verification of the capillary formula, as a value of the R115 is reduced, a value of the H300 is increased. That is, as the channel of the capillary liquid storage unit 120 is thinner, the height of the pigment column H300 is higher, and more pigments may be carried. Therefore, the needle may not dip the pigments frequently, the tattooing may be performed continuously and efficiently.

Figure 5C:
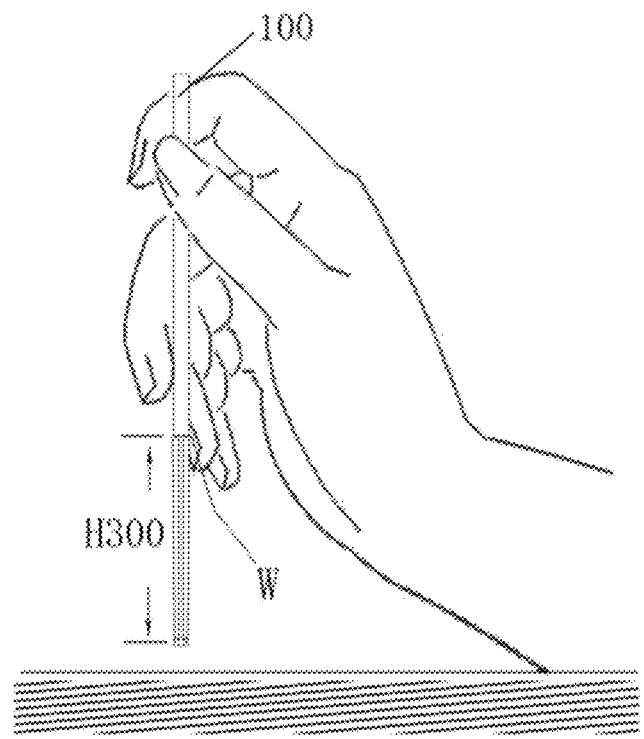
FIG. 5(c) is a schematic view showing a state of the introduction needle in FIG. 5(a), which has intaken the ink, piercing into the skin, according to an embodiment of the present disclosure.

In an embodiment, the liquid guiding member 110 of the introduction needle 100 is made of polycarbonate. Based on precision of the main production process in the art, the radius of the channel of the capillary liquid storage unit 120 may be made to have a precision of 0.1 mm, and the height of the pigment column H300 may be more than 100 mm. However, as shown in FIG. 5(c), according to a conventional way that the operator holds the introduction needle 100 by hand and a measurement of dimensions of a general human hand, a lowest position W of the introduction needle 100 that is held by the hand is generally not more than 50 mm from the needle tip. Therefore, the height H300 of the channel of the capillary liquid storage unit 120 arranged on the introduction needle 100 in the present embodiment is <50 mm.

Figure 2:
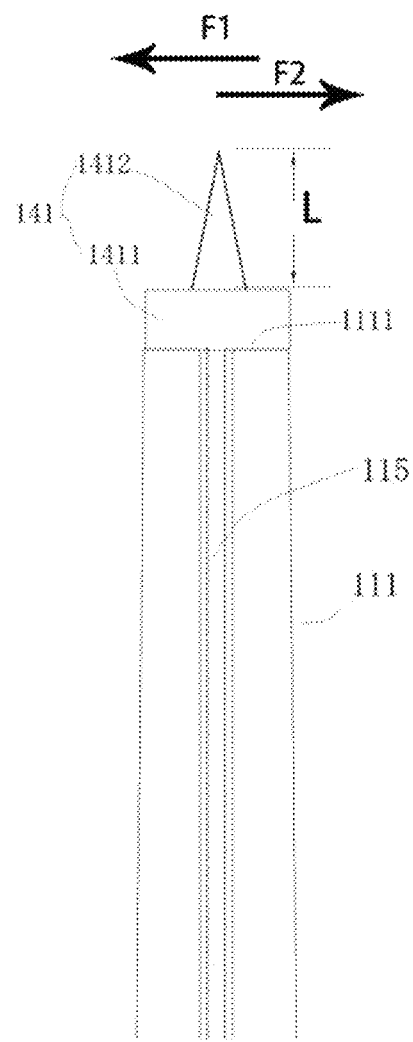
FIG. 2 is a structural schematic view of a liquid guiding post and a piercing projection according to an embodiment of the present disclosure.
Figure 4E:
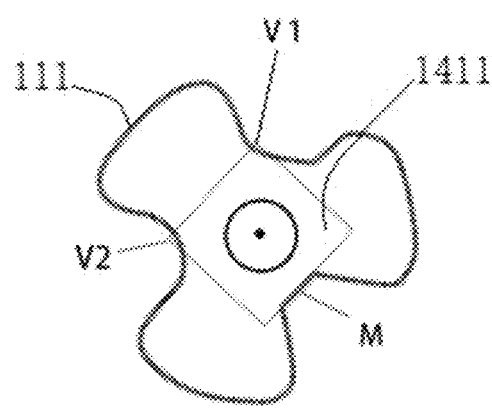
FIG. 4(e) is a schematic view of the introduction needle according to another embodiment of the present disclosure.

As shown in FIG. 2, in an embodiment, in order to achieve the better effect of guiding the pigments, the liquid guiding post 111 is fixed, by adhering, to the substrate 1411 of the piercing projection 141. As shown in FIG. 4(e), at least one corner V1, V2, and/or an edge M of the substrate 1411 on which the piercing projection 1411 is arranged is aligned with (infinitely approach) an edge of the outer wall of the liquid guiding post 111.

In an embodiment, the substrate 1411 of the piercing projection 141 is disposed at a middle of an end face of the liquid guiding member 110, and a distance from the edge of the outer wall of the liquid guiding member to one corner or one edge of the substrate is not more than 0.18 mm. That is, in an embodiment, the substrate may be disposed at a center of the first end face. However, in order to achieve the better effect of guiding the pigments, a distance from the edge of the outer wall of the liquid guiding member to one corner or one edge of the substrate is not more than 0.18 mm.

Figure 7A:
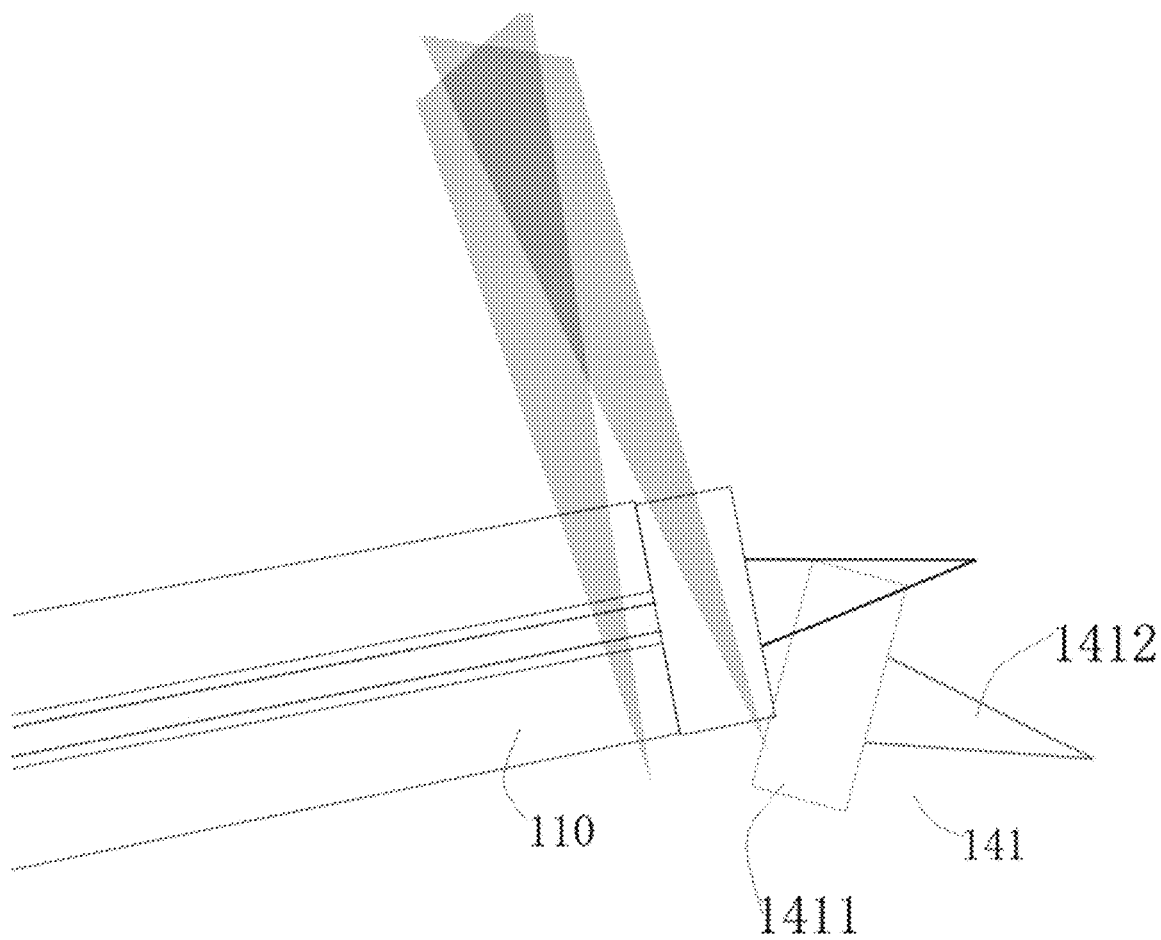
FIG. 7(a) is a schematic view showing a state of destroying an introduction needle after being used according to an embodiment of the present disclosure.

As shown in FIG. 7(a), for the introduction needle in the present embodiment an adhesive seam is defined between the liquid guiding member 110 and the piercing projection 141. After use, the introduction needle 100 may be functionally destroyed by separating, by any sharp instrument, the liquid guiding member 110 from the piercing projection 141.

Embodiment 3

In an embodiment, FIG. 1(a) shows an introduction needle 100, and a depth that the introduction needle 100 pierces into the skin from a single point, may be accurately predefined. The introduction needle 100 includes a liquid guiding member 110, a needle piercing portion 140, and a channel 115 defined in an outer wall of the liquid guiding member 110. The channel 115 serves as a capillary liquid storage unit 120.

In an embodiment, as shown in FIG. 4(a), the liquid guiding post 111 includes three metal filaments ZC1, ZC22, and ZC3 that are cut flat. The metal filaments ZC1, ZC22, ZC3 are adjacent to each other and are not fixedly connected to each other. A gap between the filaments has a capillary effect and serves as the capillary liquid storage unit. In an embodiment, the liquid guiding post 111 is fixedly connected to the connecting rod 112. The liquid guiding post 111 is welded and fixed to the substrate 1411 of the piercing projection 141.

In an embodiment, as shown in FIG. 3(a) and FIG. 3(b), the needle tooth 1412 of the present disclosure includes a tail pin and a top pin integrally formed with an end of the tail pin. The tail pin may be columnar, and the top pin may be protruding from the tail pin. A size of a cross sectional area of the top pin decreases in a direction extending from the tail pin to a free end of the top pin away from the tail pin, and the other end of the columnar tail pin is fixedly connected to the substrate.

In an embodiment, as shown in FIG. 4(b), the edge of the outer wall of the liquid guiding post 111 is aligned with (indefinitely approach) at least one corner J1, J2, J3 of the substrate 1411 and/or with one edge P of the substrate 1411.

Figure 7B:
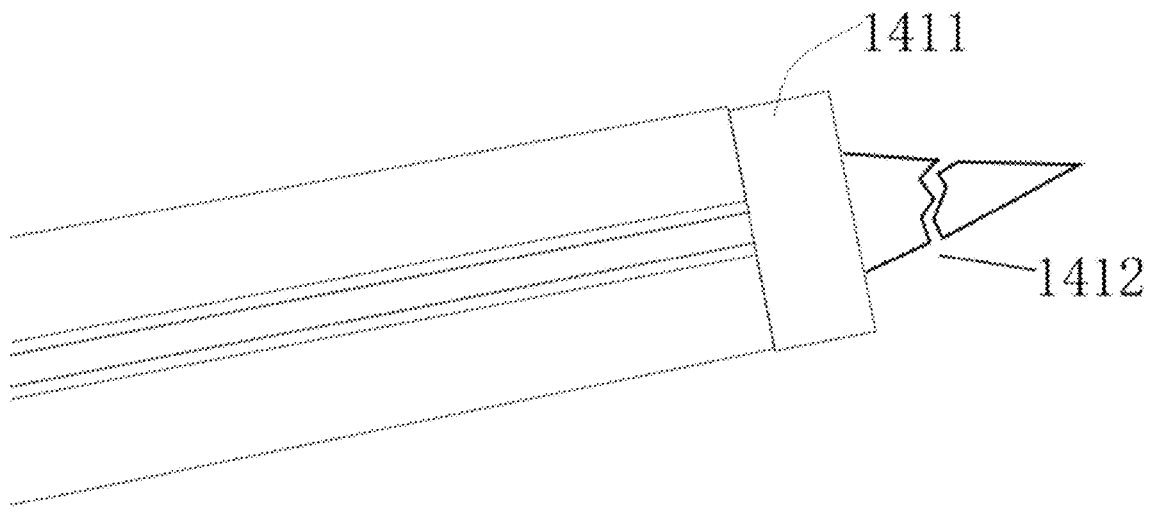
FIG. 7(b) is a schematic view showing a state of destroying an introduction needle after being used according to another embodiment of the present disclosure.

In an embodiment, the liquid guiding post 111 is welded and fixed to the piercing projection 141 of the introduction needle 100, in the present embodiment. The piercing projection 141 is made of monocrystalline silicon. After usage, the introduction needle 100 may be functionally destroyed by knocking, by any sharp instrument, off the needle tooth 1412. The destroyed introduction needle may be shown as FIG. 7(b).

Figure 1D:
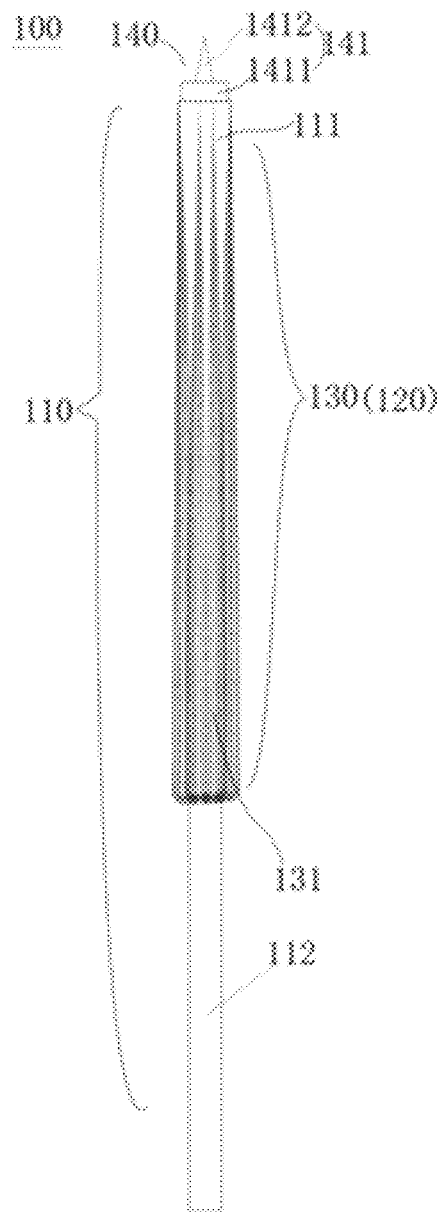
FIG. 1(d) is another structural schematic view of an introduction needle according to an embodiment of the present disclosure.

FIG. 1(d) shows an introduction needle 100, and a depth that the introduction needle 100 pierces into the skin from a single point, may be accurately predefined. The introduction needle 100 includes a piercing projection 141, a liquid guiding post 111, and a capillary liquid storage unit 120. The piercing projection 141 includes one needle tooth 1412 and a substrate 1411. A depth that the needle tooth 1412 pierces into the skin may be predefined, and the needle tooth 1412 is mounted on the substrate 1411. The needle tooth 1412 is a protrusion protruding from the substrate 1411. A size of a cross sectional area of the protrusion decreases along a direction that the needle teeth piece into the skin. For example, the size of the cross sectional area of the protrusion decreases in a direction from the substrate 1411 towards a free end of the protrusion. For example, the needle tooth may be conical. The substrate 1411 and the needle tooth 1412 are configured as a one-piece and integral structure. The substrate 1411 limits the depth that the needle tooth 1412 pierces into the skin. In an embodiment, as shown in FIG. 1(d), the liquid guiding post 111 is a strip. A fibrous substance may be attached to the outer wall of the liquid guiding post 111. A gap in a body of the fibrous substance and a gap between the body of the fibrous substance and the outer wall of the liquid guiding post 111 cooperatively serve as the capillary liquid storage unit 120.

Embodiment 4

As shown in FIG. 4(c), in an embodiment, the liquid guiding post 111 may have a first end face 1111 and a second end face 1112. The central axis of the liquid guiding column 111 extends through a center of the first end face 1111 and a center of the second end face 1112. The liquid guiding column 111 may be a column in any shape, such as a cylinder, a quadratic column, a cone-like column (or a circular truncated cone), an irregular column, and so on.

As shown in FIG. 1(*a*), a side face of the substrate 1411 is fixed to the first end face 1111 of the liquid guiding post 111 (the substrate may be adhered to and fixed to the first end face). The connecting rod 112 may be fixedly or detachably connected to the second end face 1112 of the liquid guiding post 111. The connecting rod 112 may be a column or in other shapes. The connecting rod 112 is substantially configured to connect the liquid guiding post 111 to the drive portion.

In an embodiment, a shape of the liquid guiding post 111 of the present disclosure may be arbitrary, as long as any one of the following conditions is met.

For a condition 1, a shape of the first end face 1111 is the same as a shape of the second end face 1112, and a size of the first end face 1111 is the same as a size of the second end face 1112.

For a condition 2, the shape of the first end face 1111 is the same as the shape of the second end face 1112, and the size of the first end face 1111 is less than the size of the second end face 1112.

For a condition 3, the shape of the first end face 1111 is different from the shape of the second end face 1112, and the size of the first end face 1111 is less than the size of the second end face 1112.

Based on the above conditions, the most basic characteristics of the liquid guiding member 110 is that the liquid guiding member 110 is a column. As long as the liquid guiding member 110, when being vertically disposed, may guide and direct liquid to flow, the shape of the liquid guiding member 110 is arbitrary. The shape of the liquid guiding member 110 may be determined based on the operator's demands. The accompanying drawings, which show that the shape is columnar and conical-like, are for illustrating the structure of the liquid guiding member only, and shall not be interpreted as limiting the shape of the shape of the liquid guiding member 110.

In an embodiment, the axial length of the liquid guiding post 111 is greater than a length of the longest edge or a diameter of a cross section of the first end face 1111 of the liquid guiding post 111. That is, the liquid guiding post 111 of the present disclosure is preferably an elongated column.

In an embodiment, the axial length of the liquid guiding post 111 is at least two times of the length of the shortest edge or the diameter of the first end face 1111 of the liquid guiding post 111, and the axial length of the liquid guiding post 111 is greater than the length of the longest edge or the diameter of the first end face 1111. When this length-to-diameter ratio is met, the shape of the liquid guiding member 110 is standardized, and the elongated liquid guiding member 110, when being vertically disposed, provides a better liquid guiding and storage effect.

Embodiment 5

In the tattoo process, the tattoo ink 300 (or dye) may be introduced into a superficial layer of the skin through the tattoo tool. The tattoo tool in the art may not adsorb, when being submerged into the ink 300, a large amount of ink 300. In a process that the tool pierces into the skin highly frequently, the amount of ink in the tattoo tool does not reach the amount of ink required for one piercing stage. Therefore, a high rate of empty needle during piercing may be caused. In order to improve the above mentioned defects of the tattoo tool in the art, the liquid guiding member 110 of the introduction needle in the present disclosure is improved to meet the amount of ink required for one tattoo process. The structure of the liquid guiding member 110 will be described in detail below.

Figure 6:
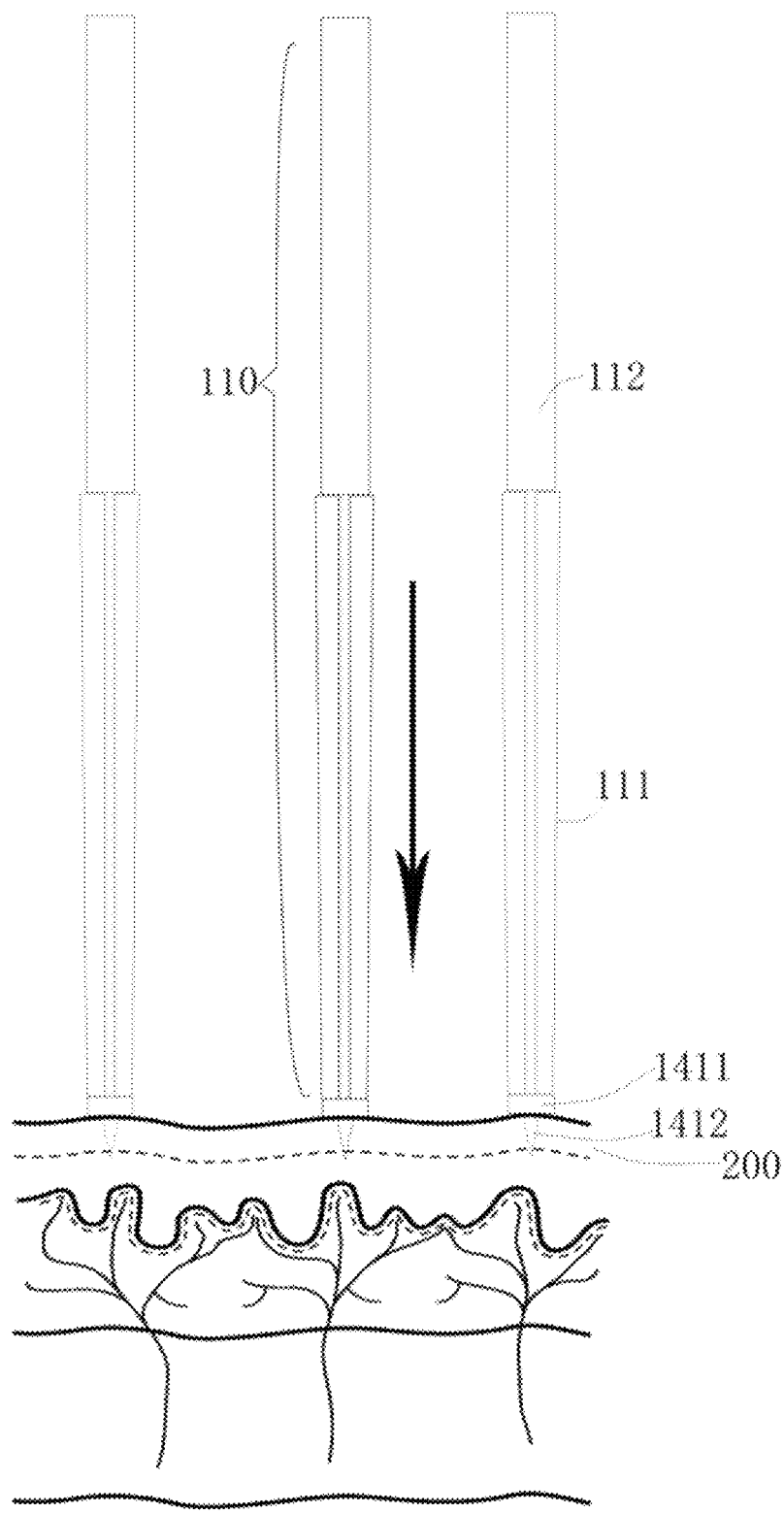
FIG. 6 is a schematic view showing a state of the introduction needle piercing into the skin according to an embodiment of the present disclosure.

As shown in FIG. 4(*a*) to FIG. 4(*d*), FIG. 5(*a*), and FIG. 6, the capillary liquid storage unit 120 is arranged in the liquid guiding post 111. Liquid stored in the capillary liquid storage unit 120 (under the gravitational force or other forces) is guided to flow to the needle piercing portion 140. The needle tooth 1412 pierces into the surface of the skin 200, and at the same time, the liquid is introduced into the surface of the skin 200 along the needle tooth 1412. The capillary liquid storage unit 120 may temporarily store the ink 300. The liquid guiding member 110 may be submerged in an ink bottle, and the capillary liquid storage unit 120 in the liquid guiding member 110 may adsorb and temporarily store the ink. When the liquid guiding member 110 carries the needle tooth 1412 of the needle piercing portion 140 to pierce into the skin, the ink 300 stored in the capillary liquid storage unit 120 is gradually guided to flow to the tip of the needle tooth 1412. In the present disclosure, the capillary liquid storage unit 120 is arranged to allow the liquid guiding member 110 to release the ink gradually, ensuring continuous supply of the ink and reducing a rate of empty needles.

According to the above embodiments, the introduction needle is required to be break into the skin during the tattoo process. Therefore, the introduction needle that has been used needs to be destroyed to prevent microbial spread caused by secondary usage. The introduction needle provided by the present disclosure has taken this into account. Therefore, as shown in FIGS. 7(*a*) to 7(*b*), the needle tooth 1412 of the introduction needle are destroyed. Alternatively, the needle piercing portion of the introduction needle is directly destroyed, and the remaining liquid guiding post 111 may be further reused.

As shown in FIG. 1(*a*) to FIG. 1(*c*), in an embodiment, the liquid guiding post 111 of the present disclosure defines a plurality of channels 115. The plurality of channels 115 extend along the axial direction of the liquid guiding member 110 and are defined in the outer wall of the liquid guiding post 111 and/or at an interior of the liquid guiding post 111. The plurality of channels 115 cooperatively serve as the capillary liquid storage unit 120. The capillary liquid storage unit 120 is substantially configured to continuously supplying ink 300 to the tip of the needle tooth 1412. Therefore, at least one of the plurality of channels 115 temporarily stores the liquid, and the liquid in the at least one of the plurality of channels 115 may be guided by the gravitational force to flow to reach the needle tooth 1412 of the needle piercing portion 140. The plurality of channels 115 may be integrally defined in the outer wall of the liquid guiding member 110 by etching, cutting, engraving and grinding, or injection molding.

As shown in FIG. 1(*a*) to FIG. 1(*c*), in an embodiment, the plurality of channels 115 are arranged on the outer wall of the liquid guiding post 111. The plurality of channels 115 serve as the capillary liquid storage unit 120. The plurality of channels 115 in the present embodiment may be objects, such as a needle filament or a needle tube, that are connected to the liquid guiding post 111 and may form a gap.

As shown in FIG. 4(*a*) to FIG. 4(*b*), in an embodiment, the liquid guiding post 111 of the present disclosure may be formed by a plurality of needle filaments 113 having flat ends and/or a plurality of small posts 114. The plurality of needle filaments 113 having the flat ends and the plurality of small posts 114 are arranged adjacent to each other. Alternatively, the plurality of said needle filaments 113 having the flat ends are arranged adjacent to each other. Alternatively, the plurality of small posts 114 are arranged adjacent to each other. A gap between two adjacent needle filaments 113 having the flat ends serves as the channel 115 which serves as the capillary liquid storage unit 120. A gap between two adjacent small posts 114 serves as the channel 115 which serves as the capillary liquid storage unit 120. A gap between one needle filament 113 having the flat end and one small post 114 serves as the channel 115 which serves as the capillary liquid storage unit 120. The needle filament or the small post 114 in the present embodiment may be solid or hollow. The capillary may be formed by the gap, which is defined by splicing the needle filaments or the small posts 114. Alternatively, the needle filament or the small post 114 may be configured to be hollow to provide an auxiliary capillary.

In an embodiment, the channel (115) extends vertically or spirally from the first end face (1111) towards the second end face (1112). An end of the channel (115) may extend through or approach the second end face (1112). The channel (115) may extend vertically along the liquid guiding post (111) to reach the first end face (1111). The channel (115) may be an annular groove defined in the outer wall of the liquid guiding post (111), and a plurality of annular grooves are spaced apart from each other and are defined in the outer wall of the liquid guiding post (111).

Embodiment 6

As shown in FIG. 1(d), the capillary liquid storage unit 120 in the present disclosure may be arranged by attaching a structure to an outside of the liquid guiding post. In the present embodiment, a liquid storage structure 130 is provided and includes one or more sheets. The sheets are attached to the outer wall of the liquid guiding post 111, and a gap is defined between the outer wall of the liquid guiding post 111 and the sheets. The gap serves as the capillary liquid storage unit 120. The capillary liquid storage unit 120 stores liquid temporarily. The liquid is guided to flow to the needle tooth 1412 of the needle piercing portion 140.

In an embodiment, the liquid storage structure 130 is formed by natural or man-made porous sheets.

In another embodiment, the liquid storage structure 130 includes a plurality of filaments. The plurality of filaments include fiber filaments 131. A gap between the plurality of fiber filaments 131 and a gap between the fiber filaments 131 and the outer wall of the liquid guiding post 111 serve as the capillary liquid storage unit 120. The capillary liquid storage unit 120 stores liquid temporarily. The liquid is guided to flow to the needle tooth 1412 of the needle piercing portion 140.

In an embodiment, the fiber filaments 131 may include animal hair, plant fiber filaments 131, chemical fiber filaments, and so on.

In an embodiment, the filaments may further include metal filaments. A gap between a plurality of metal filaments and a gap between the metal filaments and the outer wall of the liquid guiding member 110 serve as the capillary storage unit 120. The capillary storage unit 120 stores liquid temporarily, and the liquid is guided to flow to the needle tooth 1412 of the needle piercing portion 140.

In an embodiment, a position to which the liquid storage structure 130 is attached and area that the attached liquid storage structure 130 occupies may be determined based on a unit amount of ink stored in the liquid storage structure 130 and a target amount of stored ink of the liquid guiding member 110. Alternatively, the number of layers of the liquid storage structure 130 and the area of the liquid storage structure 130 may be determined based on the amount of ink used for tattoo.

Embodiment 7

The introduction needle provided in the present disclosure, serving as a tattoo tool, may introduce the tattoo ink 300 into the superficial layer of the skin. Therefore, a liquid guiding path may be formed between the ink 300 adsorbed into the liquid guiding member 110 and the needle tooth 1412 to ensure the ink 300 in the liquid guiding member 110 to flow to the tip of the needle tooth 1412 to be further introduced into the skin. Therefore, in the introduction needle of the present disclosure, one corner or one edge of at least one substrate 1411 of the piercing projection 141 needs to be disposed near the edge of the outer wall of the liquid guiding member 110. In this way, the needle tooth 1412 arranged on the substrate 1411 may receive the liquid flowing from the liquid guiding member 110. The above structure is necessary to effectively define the liquid guiding path to reduce the rate of empty needles. As shown in FIG. 4(b) and FIG. 4(d), the outer edge of the substrate 1411 of the piercing projection 141 has a portion that is substantially aligned with the outer edge of the liquid guiding post 111. The aligned portion ensures that the ink in the liquid guiding post 111 may flow to the tip of the needle tooth 1412. Similar structures are shown in FIG. 17(a) to FIG. 17(b) or FIG. 18(a) to FIG. 18(b).

In an embodiment, one corner or one edge of the substrate 1411 of the piercing projection 141 is substantially aligned with the edge of the outer wall of the liquid guiding member 110.

In another embodiment, the substrate 1411 of the piercing projection 141 is disposed at a middle of an end face of the liquid guiding member 110, and the corner or the edge of the substrate 1411 is no more than 0.18 mm away from the edge of the outer wall of the liquid guiding member 110.

Embodiment 8

Figure 8:
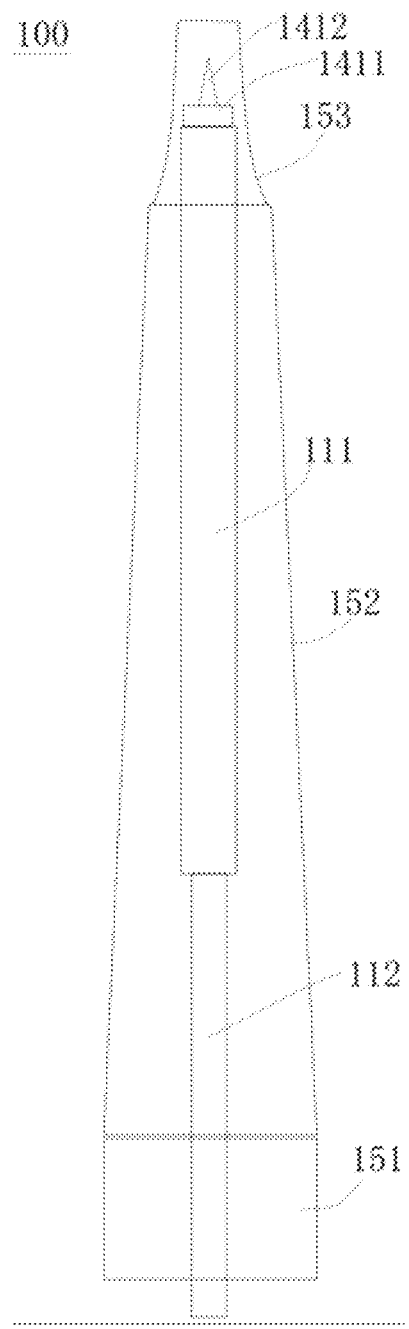
FIG. 8 is a schematic view of the introduction needle according to an embodiment of the present disclosure, wherein the introduction needle has a case.
Figure 9:
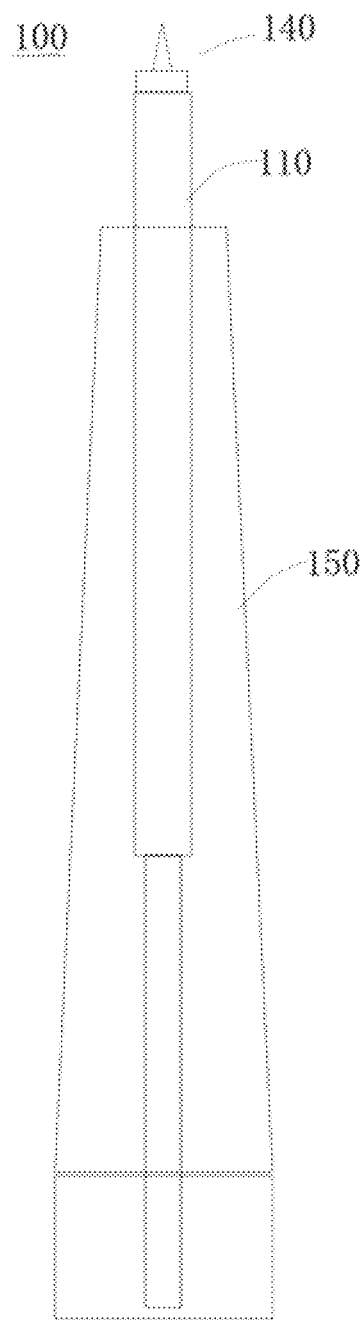
FIG. 9 is a schematic view of the structure shown in FIG. 8, wherein a needle outlet end of the case is omitted.
Figure 10:
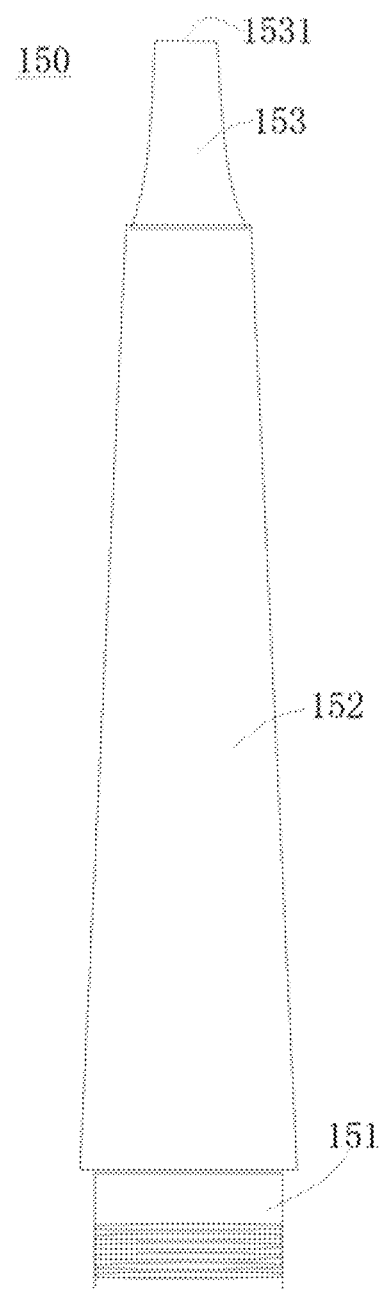
FIG. 10 is a schematic view of the case according to an embodiment of the present disclosure.

As shown in FIG. 8 to FIG. 10, the introduction needle of the present disclosure may further be arranged with a case 150. The liquid guiding member 110 is arranged inside the case 150. The liquid guiding member 110 may move reciprocately inside the case 150 to achieve the piercing operations.

In an embodiment, the case 150 of the present disclosure may be a tubular cylinder. As shown in FIG. 10, the case 150 may have a fastening end 151, an intermediate connecting tube 152, and a needle outlet end 153. The fastening end 151, the intermediate connecting tube 152, and the needle outlet end 153 are connected to each other sequentially to define a channel for the liquid guiding member 110 to move reciprocately. Each of a central axis of the fastening end 151 and a central axis of the intermediate connecting tube 152 coincides with a central axis of the case 150.

In an embodiment, the fastening end 151 of the present disclosure is detachably connectable to an external drive member (such that the introduction needle may be replaced easily). The needle outlet end 153 defines a needle outlet port 1531. The needle tooth 1412 moves reciprocately at a location near the needle outlet port 1531. The liquid guiding member 110 and the needle piercing portion 140 disposed at an end of the liquid guiding member 110 are mounted, along the central axis of the case 150, in the intermediate connecting tube 152 of the case 150. The needle piercing portion 140 is disposed near the needle outlet end 153. The liquid guiding member 110 moves reciprocately in the intermediate connecting tube 152. Further, the liquid guiding member 110 drives the needle tooth 1412 of the needle piercing portion 140 to move out of the needle outlet port 1531 or to move to be retracted into needle outlet port 1531. It will be understood that the needle tooth 1412 may alternatively be slightly retracted and disposed outside of the needle outlet port 1531.

In an embodiment, the needle outlet end 153 of the case 150 of the present disclosure may be tubular.

The needle outlet port 1531 may have a flat port or a sloped port.

In the case that the needle outlet port 1531 is the flat port, when the liquid guiding member 110 moves freely and reciprocately at the needle outlet port 1531 of the needle outlet end 153 of the case 150, a gap between the outer wall of the liquid guiding member 110 and an inner wall of the needle outlet end 153 serves as a combined capillary space. Liquid may be temporarily stored in the combined capillary space when the needle is intaking the liquid. The liquid temporarily stored in the combined capillary may be guided by the gravitational force to flow to the needle piercing portion 140 and may be introduced into the surface layer 200 of the skin while the needle tooth 1412 of the needle piercing portion 140 is piercing into the skin.

In the case that the needle outlet port 1531 is the sloped port, when the liquid guiding member 110 is moving freely and reciprocately at the needle outlet port 1531 at the needle outlet end 153 of the case 150, a gap between the outer wall of the liquid guiding member 110 and an inner wall of the sloped port serves as a combined capillary space. Liquid is temporarily stored in the combined capillary space when the needle is intaking the liquid. The liquid temporarily stored in the combined capillary space is guided to flow to the needle piercing portion 140 and is introduced into the surface layer of the skin while the needle tooth 1412 of the needle piercing portion 140 is piercing the skin. The outer wall of the liquid guiding member 110 may abut against the inner wall of the sloped port. In this case, the sloped port serves as a limiting plate for the liquid guiding post, allowing the liquid guiding post to be vertically piercing into the skin surface layer. In an embodiment, an angle may be formed between the central axis of the case and a plane in which the plate of the sloped port is located. When the liquid guiding member is moving, the sloped port may provide abutting for the liquid guiding member.

Embodiment 9

While performing tattoo, the introduction needle is operating at a relatively high frequency. Therefore, while the needle is piercing the skin, the needle may be deviated and skewed, resulting in needle slippage. Therefore, the present disclosure provides an introduction needle to limit the liquid guiding member 110, assisting the liquid guiding member 110 to pierce into and leave out of the skin in a straight direction, and the piercing may be accurately performed.

Figure 11A:
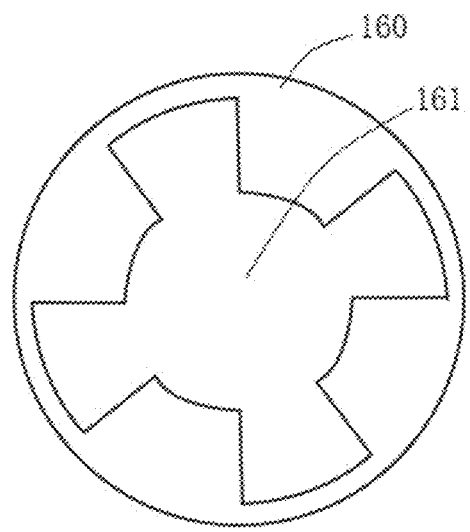
FIG. 11(a) is a cross-sectional view of a limiting structure according to an embodiment of the present disclosure, wherein the limiting structure is a knurled limiting hole.
Figure 11B:
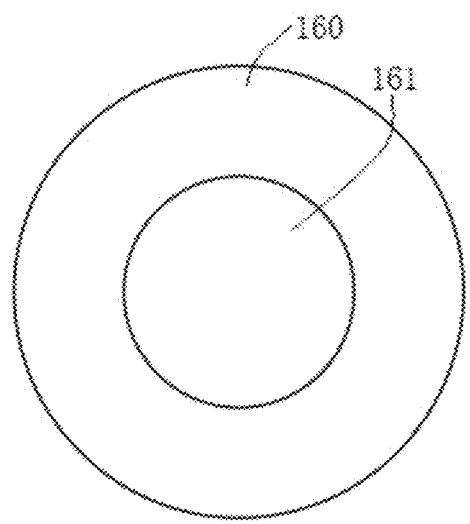
FIG. 11(b) is a cross-sectional view of a limiting structure according to another embodiment of the present disclosure, wherein the limiting structure is a circular limiting hole.

As shown in FIG. 12(*a*) to FIG. 12(*d*), FIG. 11(*a*), and FIG. 11(*b*), a limiting structure 160 is arranged inside the case 150 of the introduction needle in the present embodiment. The limiting structure 160 is disposed inside the intermediate connecting tube 152 of the case 150 and/or on the fastening end 151 of the case 150 and/or on the needle outlet end 153 of the case 150. When the liquid guiding member 110 is moving reciprocately along the central axis of the case 150, the liquid guiding member 110 may abut against the limiting structure 160. The limiting structure 160 limits the liquid guiding member 110 from swinging in a direction along a cross section of the case 150. In this way, the liquid guiding member 110 drives the needle tooth 1412 of the needle piercing portion 140 to vertically move out of the case 150 to pierce into the skin surface 200. Further, the liquid guiding member 110 drives the needle tooth 1412 of the needle piercing portion 140 to vertically move from the outside of the needle outlet port 1531 to the inside of the case 150. It will be understood that the needle tooth 1412 may alternatively be slightly retracted and still located outside the case 150.

In an embodiment, the limiting structure 160 of the present disclosure may be a limiting hole 161. The limiting hole 161 may be a through hole. A central axis of the through hole may or may not coincide with the central axis of the liquid guiding member 110. Preferably, the central axis of the through hole does not coincide with the central axis of the liquid guiding member 110. An inner diameter of the through hole may be adapted to an outer diameter of the liquid guiding member 110. For example, a shape and a size of the central through hole may be adapted to a shape and a size of the largest cross section of the liquid guiding member 110. The adaptation in this case may not refer to the shape and the size of the through hole being identical to the shape and the size of the largest cross section of the liquid guiding member, but allows the liquid guiding member to pass through the through hole. In an embodiment, a cylindrical liquid guiding member may be adapted with a square through hole. In this case, a gap between the cylindrical liquid guiding member and the square through hole may provide the capillary effect to store the liquid, ensuring the liquid guiding member 110 to move straight in the central through hole (the limiting structure provides abutting to the liquid guiding member to limit the liquid guiding member from swinging in a lateral direction and to ensure the liquid guiding member to move straight in central through hole). In this way, the central through hole limits a position of the liquid guiding member 110. The central through hole may be circular or irregularly shaped. As shown in FIG. 11(*a*), when the through hole is irregularly shaped, the through hole may be suitable for various shapes of liquid guiding members.

Figure 25:
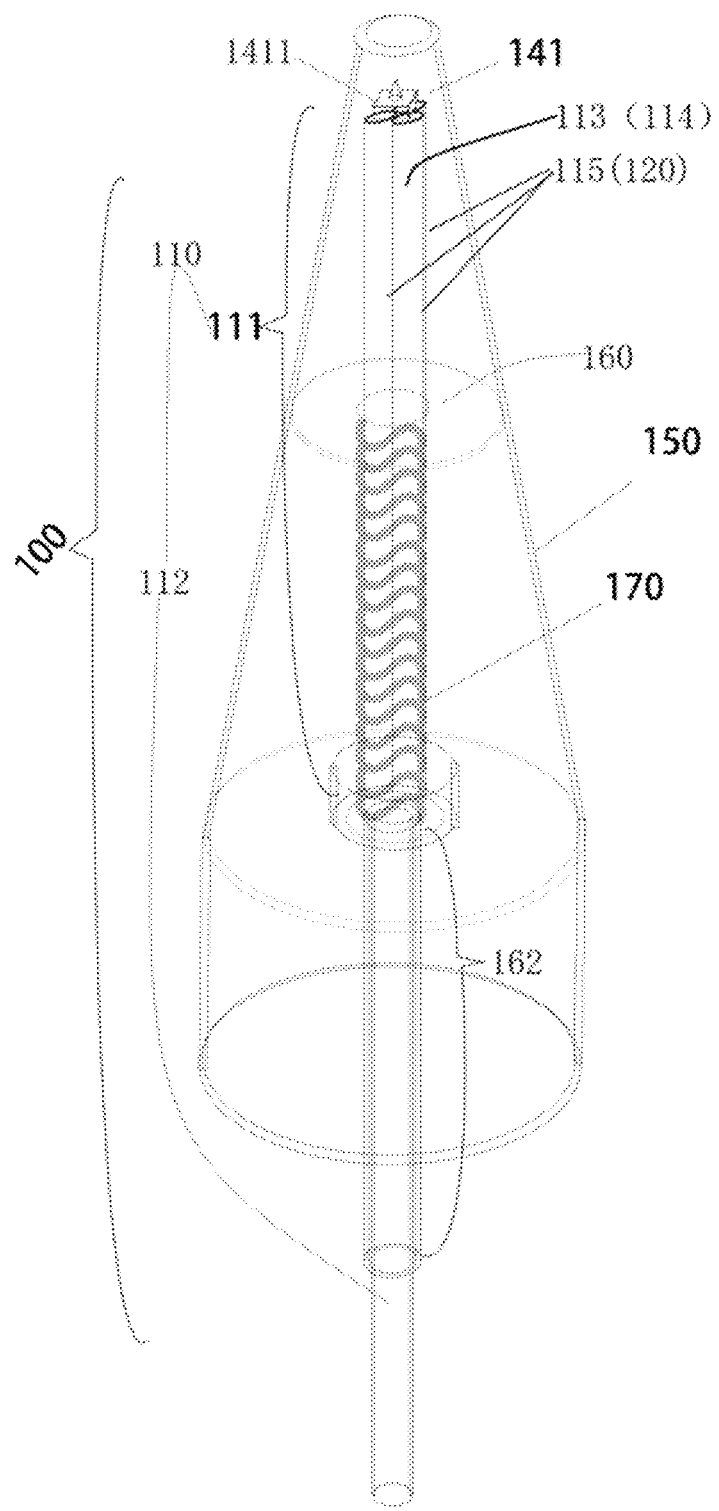
FIG. 25 is a structural schematic view of the introduction needle according to an embodiment of the present disclosure.

In an embodiment, as shown in FIG. 25, the limiting structure 160 of the present disclosure may be a limiting tube 162. The limiting tube 162 has a channel. A central axis of the channel may or may not coincide with the central axis of the liquid guiding member 110. An inner diameter of the channel is adapted to the outer diameter of the liquid guiding member 110. A shape and a size of the channel are adapted to the shape and the size of the largest cross section of the liquid guiding member 110. The adaptation in this case may not refer to the shape and the size of the channel being identical to the shape and the size of the largest cross section of the liquid guiding member, but allows the liquid guiding member to pass through the channel. In an embodiment, the cylindrical liquid guiding member may be adapted with a square channel. In this case, a gap between the cylindrical liquid guiding member and the square channel may provide the capillary effect to store the liquid, ensuring the liquid guiding member 110 to move straight in the central channel. The central channel limits the position of the liquid guiding member 110.

Figure 12A:
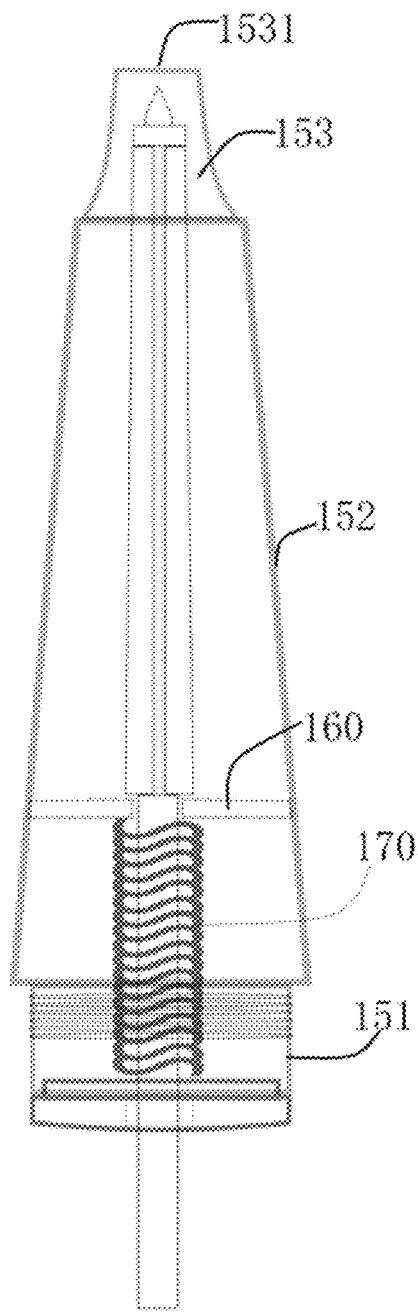
FIG. 12(a) is a structural schematic view of the introduction needle according to an embodiment of the present disclosure.
Figure 12B:
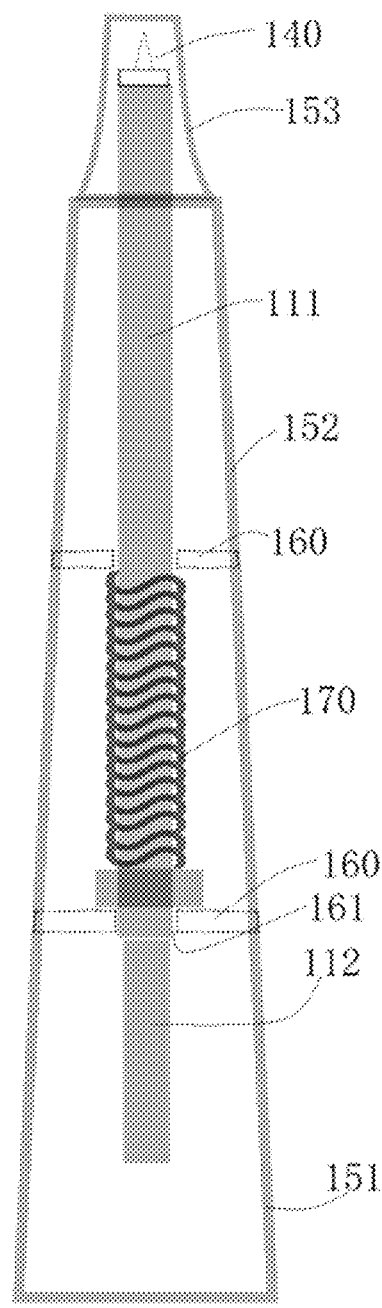
FIG. 12(b) is another structural schematic view of the introduction needle according to an embodiment of the present disclosure.
Figure 12C:
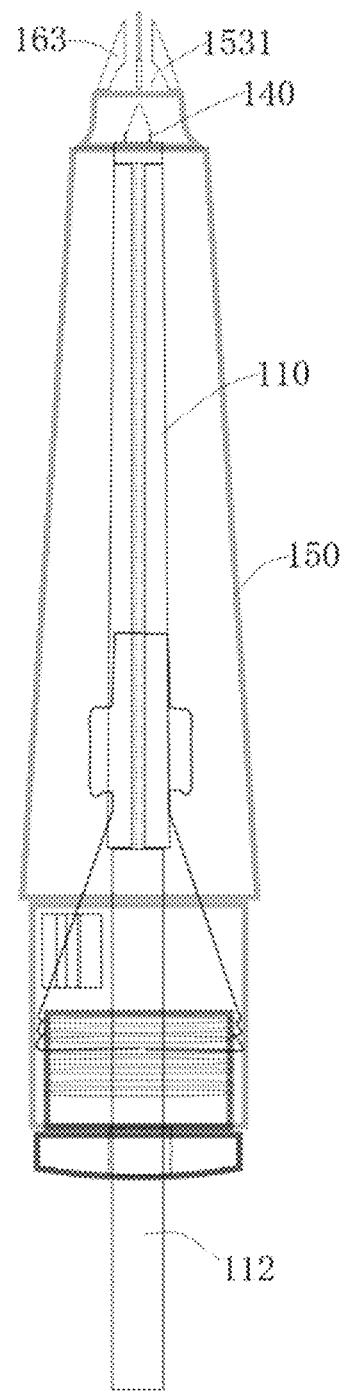
FIG. 12(c) is another structural schematic view of the introduction needle according to an embodiment of the present disclosure.
Figure 12D:
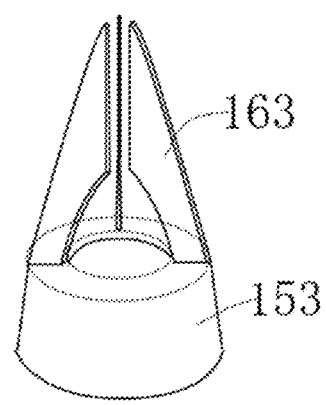
FIG. 12(d) is a perspective view of a needle outlet end of the introduction needle shown in FIG. 12(c).
Figure 12E:
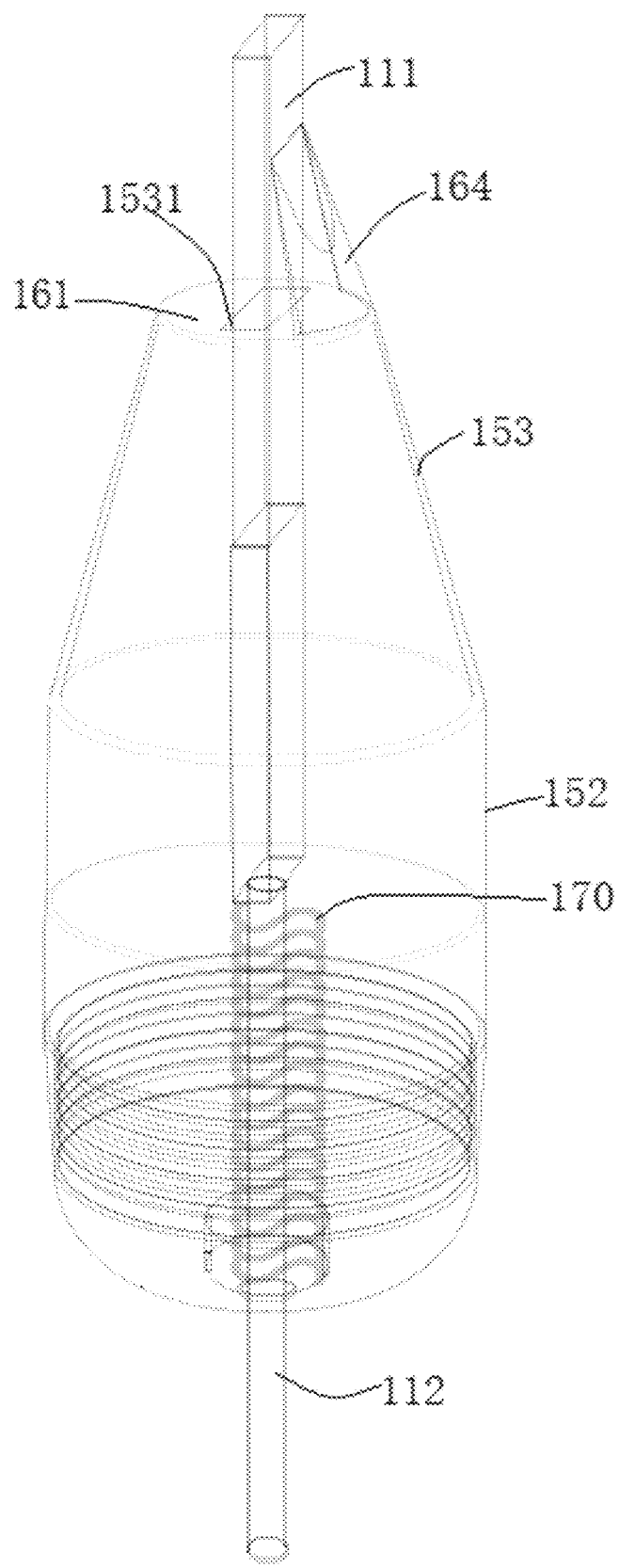
FIG. 12(e) is a structural schematic view of the introduction needle according to an embodiment of the present disclosure.
Figure 13A:
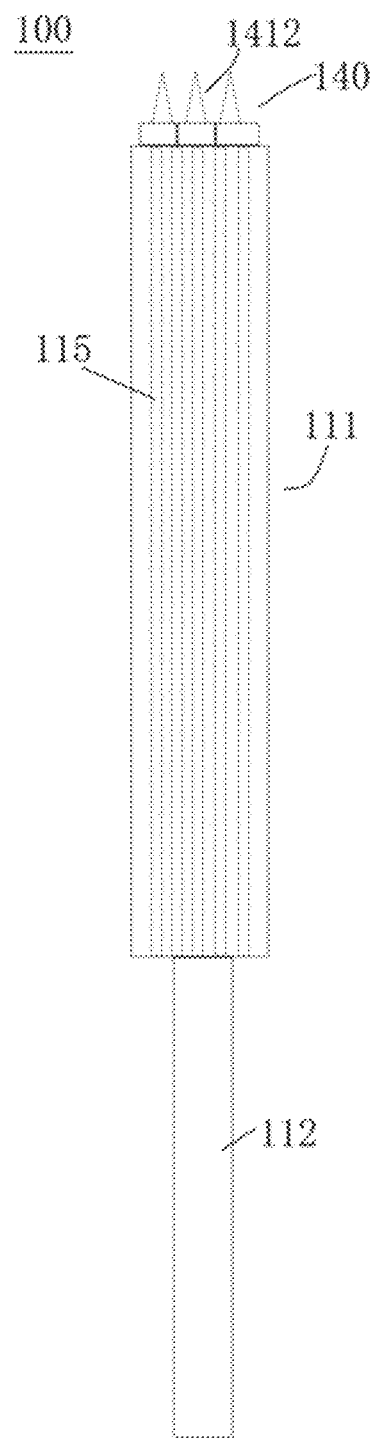
FIG. 13(a) is a structural schematic view of the introduction needle according to an embodiment of the present disclosure.
Figure 13B:
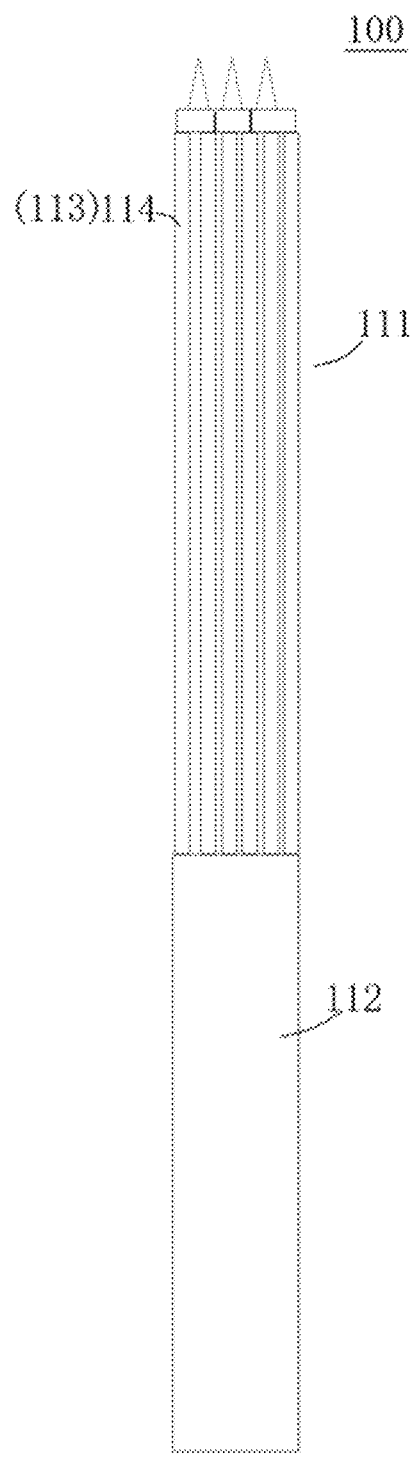
FIG. 13(b) is another structural schematic view of the introduction needle according to an embodiment of the present disclosure.
Figure 13C:
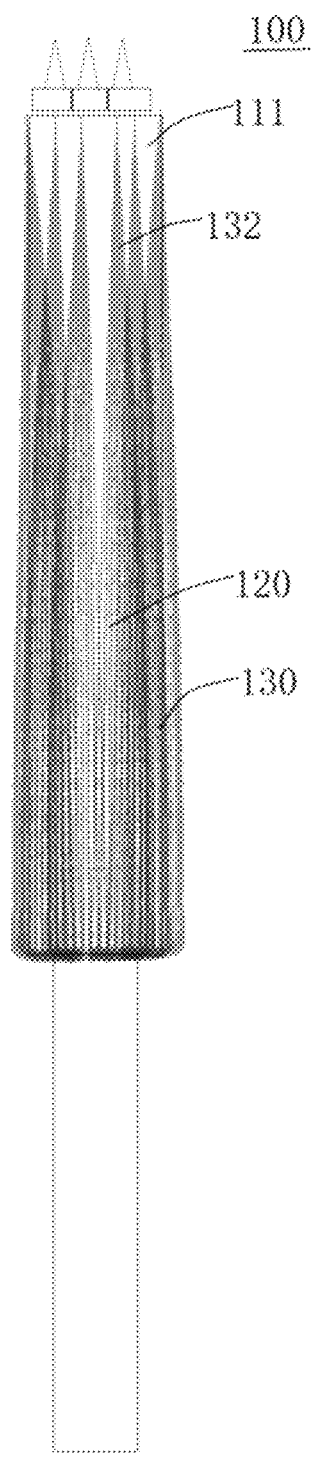
FIG. 13(c) is another structural schematic view of the introduction needle according to an embodiment of the present disclosure.
Figure 14A:
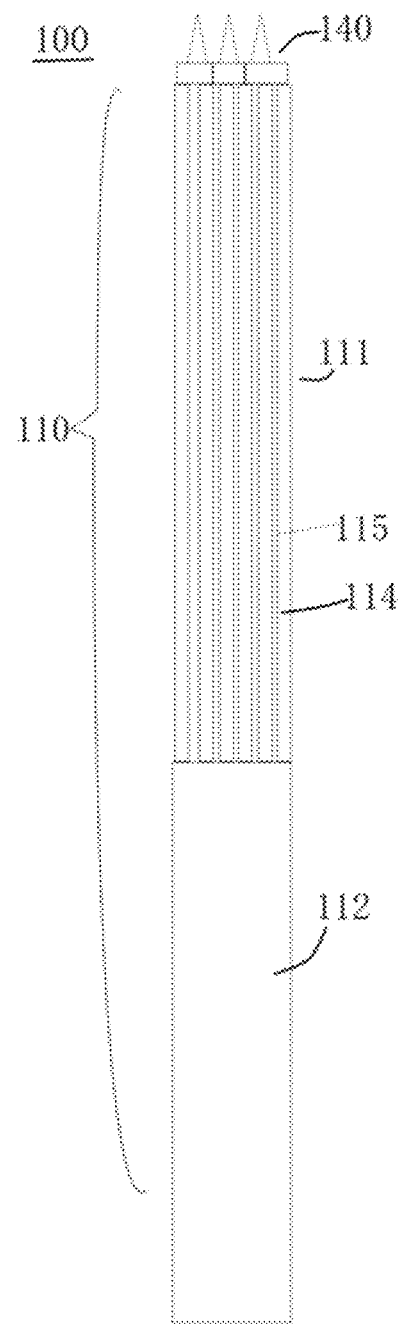
FIG. 14(a) is a structural schematic diagram of the introduction needle according to another embodiment of the present disclosure.
Figure 14B:
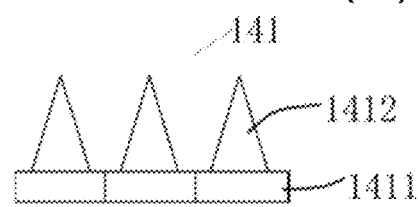
FIG. 14(b) is a planar schematic diagram of a piercing projection of a needle piercing portion according to an embodiment of the present disclosure.
Figure 14C:
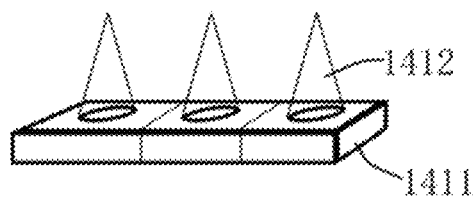
FIG. 14(c) is a perspective view of the piercing projection shown in FIG. 14(b).
Figure 15A:
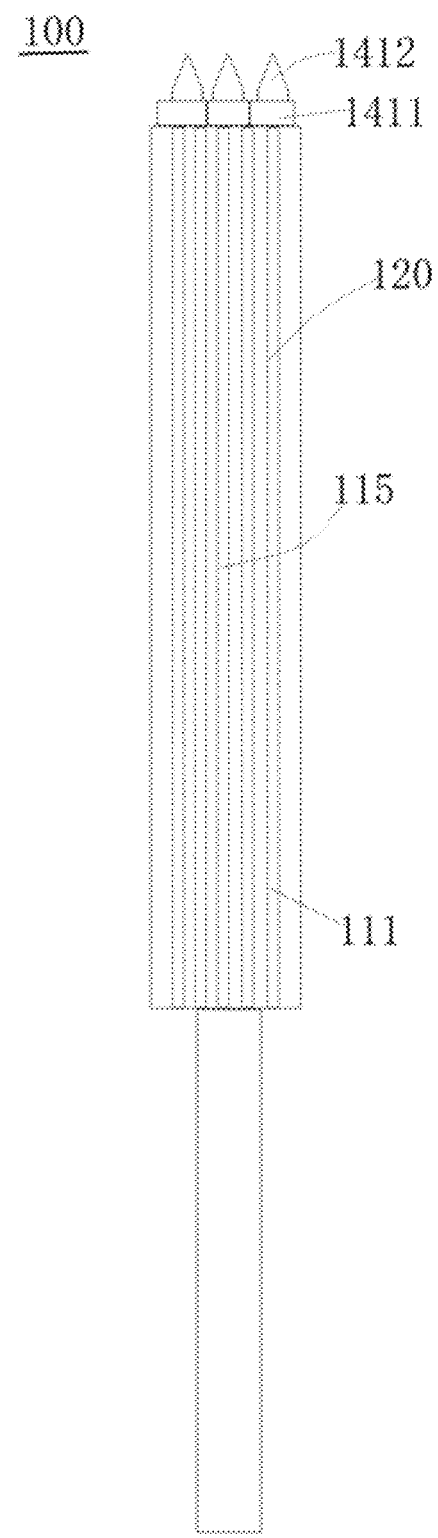
FIG. 15(a) is a structural schematic view of an introduction needle according to still another embodiment of the present disclosure.
Figure 15B:
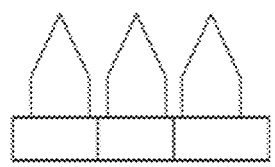
FIG. 15(b) is a planar schematic diagram of a piercing projection of a needle piercing portion according to an embodiment of the present disclosure.
Figure 15C:
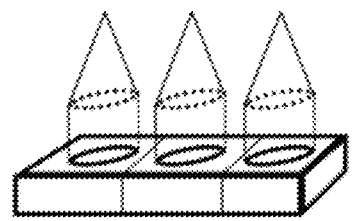
FIG. 15(c) is a perspective view of the piercing projection shown in FIG. 15(b).
Figure 16:
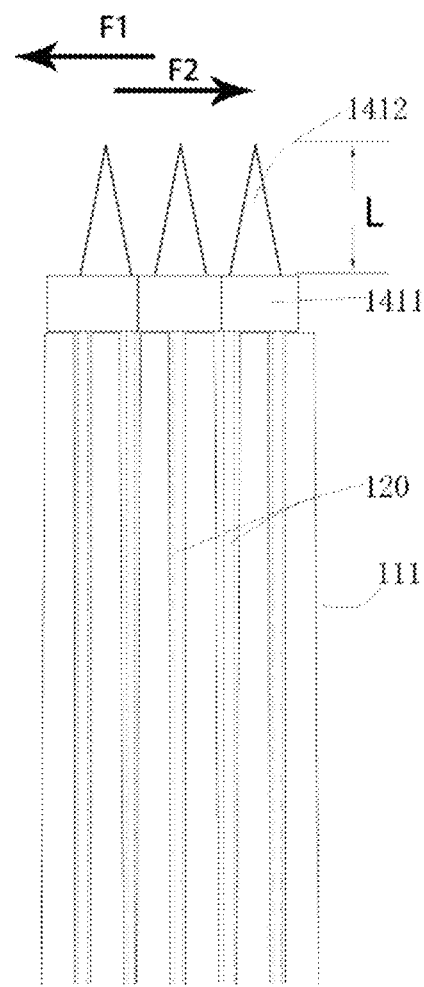
FIG. 16 is a structural schematic view of a liquid guiding post and a piercing projection according to an embodiment of the present disclosure.
Figure 17A:
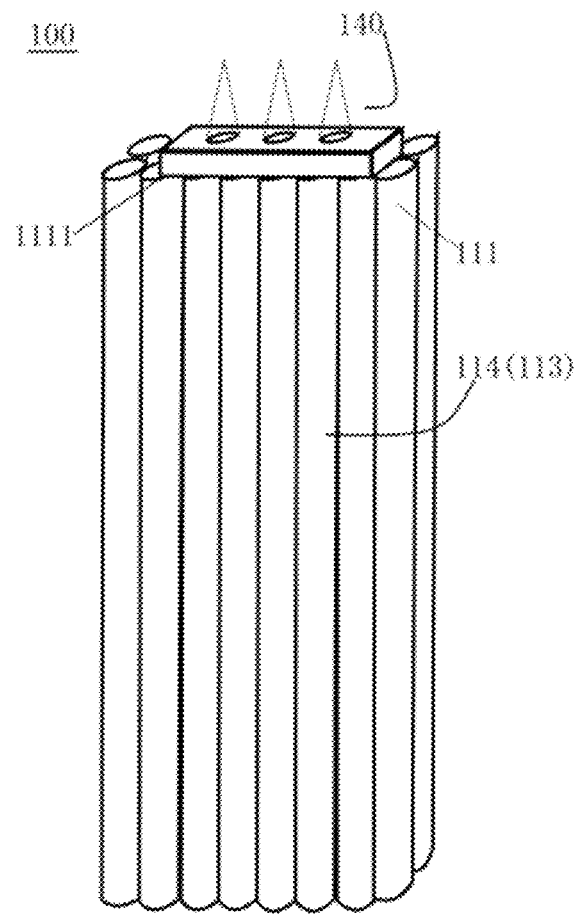
FIG. 17(a) is a perspective view of a portion of the introduction needle described according to an embodiment of the present disclosure.
Figure 17B:
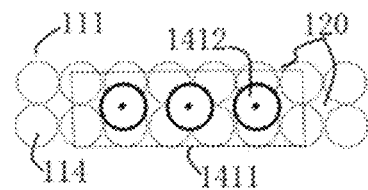
FIG. 17(b) is a planar schematic view of the introduction needle shown in FIG. 17(a), viewed from a viewing angle.
Figure 18A:
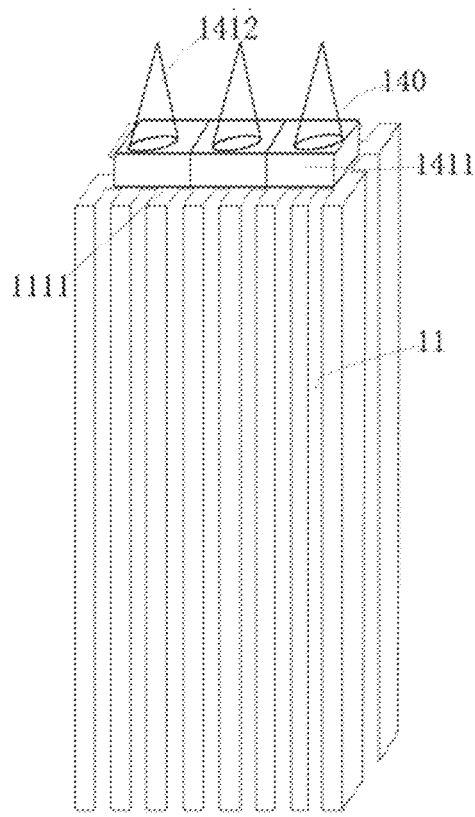
FIG. 18(a) is a perspective view of a portion of the introduction needle according to another embodiment of the present disclosure.
Figure 18B:
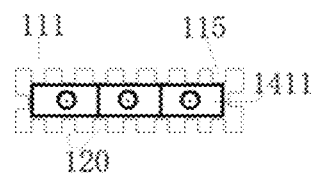
FIG. 18(b) is a planar schematic view of the introduction needle shown in FIG. 18(a), viewed from a viewing angle.

In an embodiment, as shown in FIG. 12(e), the limiting structure 160 of the present disclosure may be a limiting plate 164. The limiting plate 164 has a limiting surface. An angle is generated between a plane in which the limiting surface is located and the central axis of the liquid guiding member 110. In one case, the plane in which the limiting surface is located may be parallel to the central axis of the liquid guiding member 110. When the liquid guiding member 110 is moving reciprocately along the central axis of the case 150, the liquid guiding member 110 abuts against the limiting surface. The limiting surface limits the liquid guiding member 110 from swinging in the direction of the cross section of the case 150. The limiting plate 164 of the present disclosure may be disposed at the needle outlet port 1531 of the needle outlet end 153 of the case 150. One or more limiting structures 164 may be arranged. When more than one limiting structures 164 are arranged, the more than one limiting structures 164 may be evenly distributed at the needle outlet port 1531 to define a channel, and the needle piercing portion 140 may move straight in and out of the channel.

As shown in FIG. 12(c) and FIG. 12(d), in an embodiment, the limiting structure 160 of the present disclosure may be a limiting bracket 163. The limiting bracket 163 is disposed at an end of the case 150 (or disposed inside the case). The limiting bracket 163 includes one or more sub-brackets. For each of the one or more sub-brackets, a side of the sub-bracket abuts against the liquid guiding member 110. The sub-brackets limit the liquid guiding member 110 from swinging in the direction of the cross section of the case 150. When the liquid guiding member 110 moves reciprocately along the central axis of the case 150, the liquid guiding member 110 abuts against a side of the sub-bracket. Further, due to abutting against the side of the sub-bracket, the liquid guiding member 110 is guided to move to the needle outlet port 1531 of the case 150.

The limiting structure 160 in the present embodiment may effectively limit and guide the liquid guiding member 110, ensuring the needle to pierce the skin at desired position accurately and preventing the needle from being skewed or from slipping.

Embodiment 10

As shown in FIG. 12(a) to FIG. 12(c), the introduction needle 100 in the present embodiment may further include an elastic member 170, such as a spring, a silicone member, or a rubber band. An end of the elastic member 170 is connected to the case 150, and the other end of the elastic member 170 is connected to the connecting rod of the liquid guiding member 110. The elastic member may be connected to the case or the liquid guiding member in various ways, such as connection by abutting, encased connection, or connection by hooks, and so on. The case 150 is connected to the motorized rod. When the liquid guiding member 110 is driven by an external force (a motor of the motorized rod is activated to apply a driving force to the liquid guiding member 110) to move along the central axis of the case 150 towards the needle outlet port 1531 of the case 150, the elastic member 170 is elastically deformed to drive the liquid guiding member 110 to move back to its initial position.

Embodiment 11

Different tattoo patterns and tattoo locations may require different tattoo needles to be used. The present disclosure further provides an introduction needle 100, and the piercing projection 141 of the introduction needle includes one or more substrates 1411. One needle tooth 1412 is arranged on each of the one or more substrates 1411. The one or more substrates 1411 are arranged into one row, and therefore, the corresponding needle teeth 1412 arranged on the corresponding one or more substrates 1411 are also arranged into one row.

As shown in FIG. 13(a) to FIG. 13(c), FIG. 14(a) to FIG. 14(c), and FIG. 15(a) to FIG. 15(c), for one introduction needle, more than one needle teeth are arranged in a row. This type of introduction needle may be configured to produce a tattoo having a relatively long linear pattern and a small transition arc. Compared to the introduction needle having a single needle tooth, the introduction needle having more than one needle teeth in the present embodiment may produce specific patterns more quickly. Of course, in order to produce a tattoo having dots or having large transition arcs between linear patterns, the introduction needle having the single needle tooth may be more advantageous.

Figure 19:
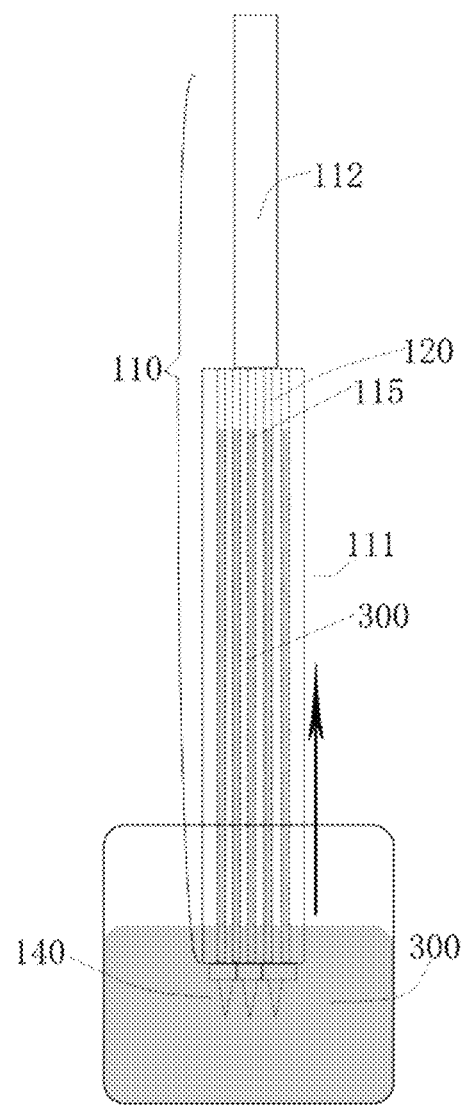
FIG. 19 is a schematic view showing a state of the introduction needle while the introduction needle is intaking ink, according to an embodiment of the present disclosure.
Figure 20:
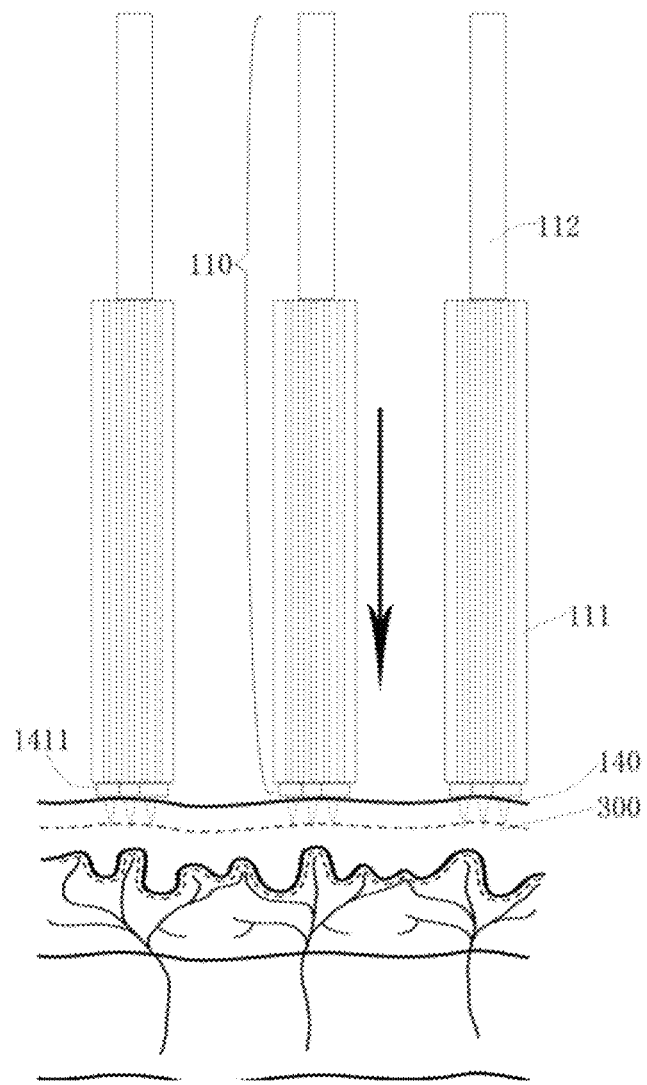
FIG. 20 is a schematic view showing a state of the introduction needle piercing into the skin, according to an embodiment of the present disclosure.

As shown in FIG. 19 and FIG. 20, FIG. 19 is a schematic view showing an in-use state of the introduction needle while intaking the ink. The needle piercing portion in the drawings has a plurality of substrates and a plurality of needle teeth. The ink in an ink bottle is adsorbed into the capillary liquid storage unit 120 from the end of the liquid guiding member. Further as shown in FIG. 20, when the introduction needle is being used to pierce into the skin, each of the plurality of substrates 1411 of the needle piercing portion 140 limits a depth that a corresponding one of the plurality of needle teeth 1412 pierces into the skin. As shown in the drawings, the plurality of needle teeth pierce into the skin at the same time. Such an arrangement of the substrates and the needle teeth allows the needle piercing portion to be more suitable for drawing lines.

Figure 21A:
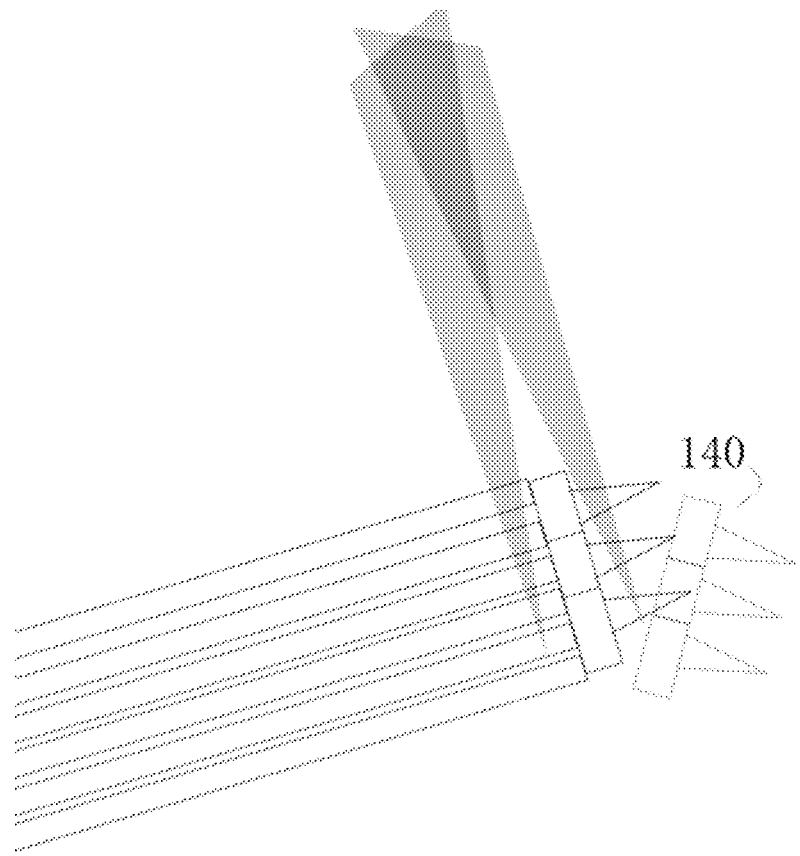
FIG. 21(a) is a schematic view showing a state of destroying an introduction needle after being used according to an embodiment of the present disclosure.
Figure 21B:
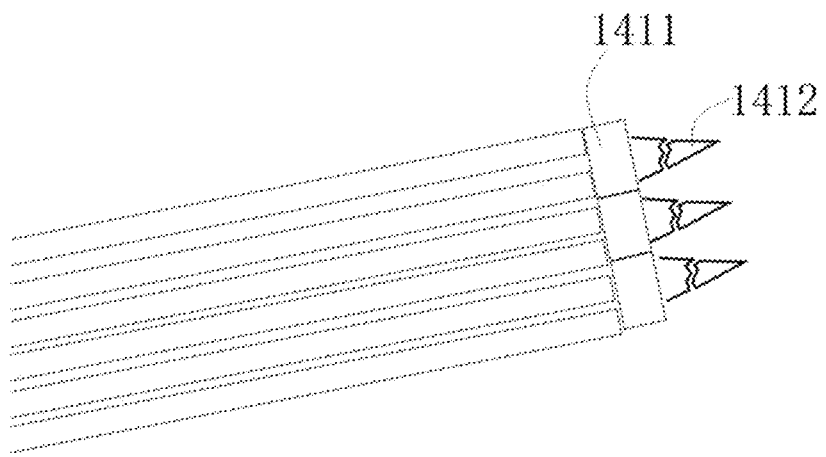
FIG. 21(b) is a schematic view showing a state of destroying an introduction needle after being used according to another embodiment of the present disclosure.

As shown in FIG. 21(a) and FIG. 21(b), the needle piercing portion having a single row of the plurality of needle teeth may also be destroyed simply.

Embodiment 12

Based on the introduction needle of the present embodiment, the present disclosure further provides a tattoo device. The tattoo device includes any one of the above-mentioned introduction needles 100 and an external drive member that drives the liquid guiding member 110 of the introduction needle 100 to move.

In an embodiment, the external drive member includes a manual rod, a motorized rod, and an intelligent arm.

The present disclosure further provides another introduction needle, which is also referred to as a tattoo needle, as shown in FIG. 26 to FIG. 39.

The tattoo needle includes a needle shell 1, a needle body 2, and a resilient member 3. The needle body 2 is arranged in the needle shell 1 and is movable along an axis of the needle shell 1. The resilient member 3 is configured to push the needle body 2 to move towards an interior of the needle shell 1. A needle head 4, which may be referred to as the needle piercing portion in the above embodiments, is mounted at a bottom of the needle body 2. For example, the needle head 4 may be the needle piercing portion (the needle tooth and the substrate) in the above embodiments, and the needle body may be the liquid guiding member in the above embodiments. The needle body is rotationally connected to the needle shell. The needle head has a multifaceted structure having a tip end 5. The tip end is located at a free end of the needle body. The multifaceted structure has 4 to 12 faces.

Figure 27:
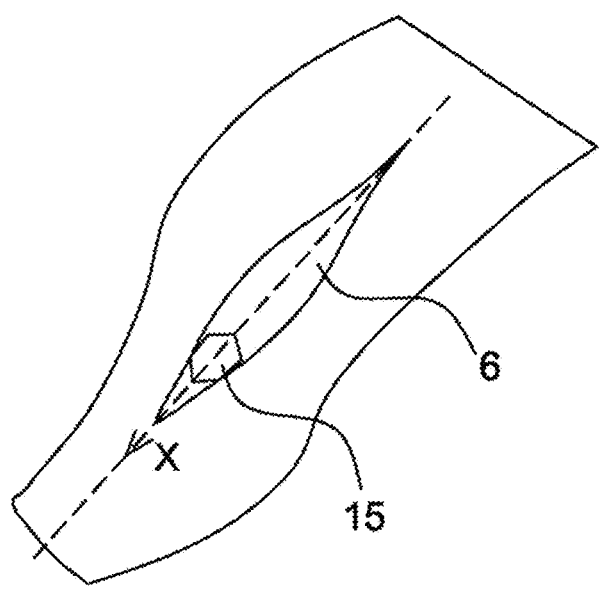
FIG. 27 is a structural schematic view of a needle piercing portion taking a sharp portion of a multifaceted structure to transversely break skin according to an embodiment of the present disclosure.
Figure 28:
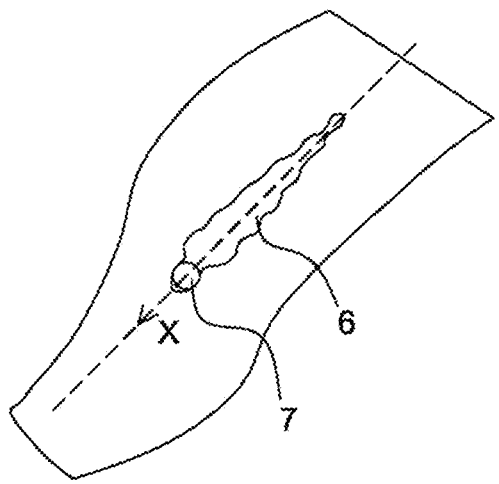
FIG. 28 is a structural schematic view of a conical needle taking a tip end to transversely break skin, in the related art.

In the present disclosure, the multifaceted structure has 4 to 12 faces. The tip end of the multifaceted structure serves as a tip end of the entire needle head. Specifically, the needle tooth includes a plurality of faces and one tip end, the one tip end points away from the substrate. Each of the plurality of faces includes one bottom edge and two side edges; the bottom edge is arranged on the substrate and the two side edges extend from two ends of the bottom edge in a direction away from the substrate. Ends of the two side edges of all of the plurality of faces away from the substrate are connected to each other to form the one tip end. In this way, when producing a tattoo, the tip end of the introduction needle pierces the skin in the vertical direction. After the skin is pierced/broken in the vertical direction, the skin needs to be broken transversely. At this moment, adjacent faces of the multifaceted structure are connected to each other to form a sharp portion. In other words, adjacent side edges of two adjacent faces of the plurality of faces coincide with each other; and the coinciding side edge form the sharp portion, and the needle head takes the sharp portion to break the skin transversely. The sharp portion has certain sharpness, which is similar to a knife blade or scissors, and can cut the skin transversely. Therefore, when the needle head takes the sharp portion to break the skin transversely, the needle head is encountered by a reduced resistance, and transverse movement of the needle head can be performed smoothly. After the skin is broken transversely, the skin is broken in a straight line. As shown in FIG. 27, a generated cut of the skin is smoother and has a better appearance, and therefore, colors during tattooing may be retained better. As shown in FIG. 27, FIG. 27 is a structural schematic view of the needle piercing portion taking the sharp portion of the multifaceted structure to transversely break skin. The dashed line in the drawing is a track of the transverse breaking, and X is the direction of the transverse breaking. In the related art, a conventional needle head 7 is a conical structure having a tip end. When the conical structured needle head 7 is used to transversely break the skin, a side surface of the conical structure is curved, and therefore, the curved conical structure cannot transversely cut the skin. Instead, the curved conical structure takes a blunt tearing and grinding force to break the skin. In this case, when the skin is broken transversely to generate a pattern, a resistance against the cutting is large, and the tip end of the conical structured needle head needs to be taken out of the skin and pierced into the skin repeatedly to cut the skin by tearing and grinding. Therefore, the operation is complex and is less efficient. In addition, the cut of the skin 6 generated by tearing and grinding, such that a border of the cut is may be jagged, the skin may be damaged more severely, and the colors for tattooing may not be retained effectively, and any line-patterned tattoo may have a low yield. A few years later, the color may be lost, or the line pattern is broken, or the color of the pattern may be blended. As shown in FIG. 28, FIG. 28 is a structural schematic view of the conical needle in the art, taking the curved side face and the tip end to transversely break skin. The dashed line is the track of the transverse breaking, and X is the direction of transverse breaking.

The resilient member may be a spring. An upper portion of the needle body has an annular protrusion 8. An end of the spring abuts against the annular protrusion to push the needle body to move upward, i.e., to be received in the needle shell. When in use, the top of the needle shell is connected to an operation handle, and a driving mechanism of the operation handle extends and retracts repeatedly. When the driving mechanism of the operation handle extends, the driving mechanism pushes the needle body and the needle head to move downwardly, countering elasticity of the spring, such that the needle head extends out of the needle shell to break the skin for tattooing. When the driving mechanism moves upwardly, the spring is reset to push the needle body and the needle head to move upwardly to be reset and received in the needle shell. In this way, the needle head extends out and retracts reciprocally to perform tattooing.

As shown in FIG. 27, FIG. 29, FIG. 33 and FIG. 34, every two adjacent faces of the multifaceted structure are connected to each other to form the sharp portion 9. When the needle head is subjected to a transverse force (for example, when the needle head is moving transversely, the skin applies the transverse force to the needle head), the needle head and the needle body may be adaptively rotated within the needle shell to enable the sharp portion to directly face the direction from which the transverse force is applied to the needle head.

During tattooing, the top of the needle shell is connected to the operation handle, the driving mechanism of the operation handle extends and retracts repeatedly. When the driving mechanism extends, the driving mechanism pushes the needle body and the needle head to move along the axis of the needle shell to extend out of the needle shell, such that the needle head can break the skin in the vertical direction. In the present embodiment, the needle body and the needle head are rotatably connected to the needle shell and can rotate for 360° at will. Rotation (i.e., circumferential movement) of the needle body and the needle head inside the needle shell is not restricted by any structure. The needle head has the multifaceted structure, and when the needle body and the needle head are moving along the axial direction of the needle shell (i.e., moving out of the needle shell to break the skin in the vertical direction), the rotation of the needle body and the needle head inside the needle shell is irrelevant to the axial movement of the needle body and the needle head (moving out of the needle shell). Regardless of any rotation angle of the needle body and the needle head inside the needle shell, it is always the tip end of the needle head to break the skin. However, when the needle head breaks the skin transversely, the needle head is subject to a resistance in a radial direction of the needle head (i.e., the side face of the needle head receives the resistance). In this case, if a flat face is directly facing the skin (i.e., facing the direction from which the resistance is applied), the needle head may receive a quite large resistance. In the present disclosure, the needle head has the multifaceted structure, and every two adjacent faces of the multifaceted structure are connected to each other to form the sharp portion. In addition, the sharp portion has a certain angle, i.e., each face is at a certain angle with respect to its adjacent face. The sharp portion may guide the needle head to rotate, and in this way, the resistance applied to the needle head is reduced. Therefore, when the needle head is breaking the skin transversely, the cut of the skin may cause the needle head and the needle body to adaptively rotate. As a result, the needle head is rotated to enable a sharp portion that is located closest to the cut of the skin to directly face the cut of the skin, i.e., to directly face the direction from which the resistance is applied. The sharp portion may guide the needle head to move, and in addition, the sharp portion may further break the skin in the transverse direction, and the resistance against the breaking is reduced. In this way, the skin breaking and the tattooing may be performed smoothly, the tattoo pattern may be produced more smoothly and have a better appearance, and skin damage may be minimized.

Figure 29:
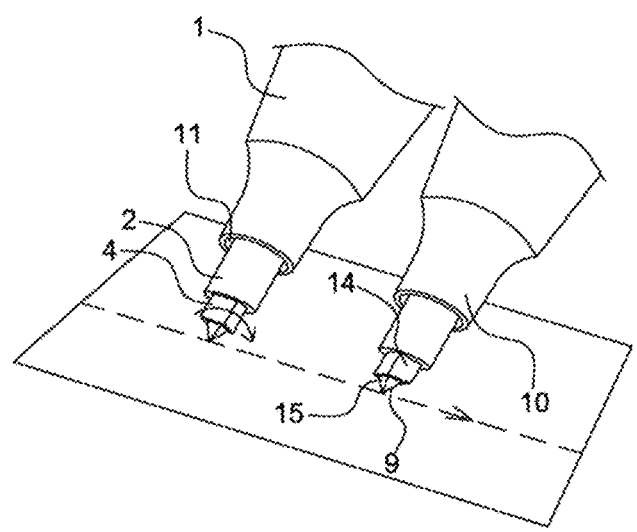
FIG. 29 is a structural schematic view of the introduction needle being adaptively rotating when transversely breaking the skin according to an embodiment of the present disclosure.

As shown in FIG. 29, FIG. 29 is a structural schematic view of the introduction needle being adaptively rotating when transversely breaking the skin according to an embodiment of the present disclosure.

In the present disclosure, the number of faces of the multifaceted structure is 4 to 12. In this way, when the needle head breaks the skin in the transverse direction, regardless of any direction in which the skin is broken, the needle head and the needle body can be quickly adaptively rotated to allow the sharp portion that is located closest to the cut side of the skin to face the direction of breaking the skin. Therefore, the introduction needle is applicable to perform any tattoo pattern, the generated tattoo may have smooth lines and a better appearance, and skin damage is minimized.

As shown in FIG. 26, FIG. 29, FIG. 32, and FIGS. 37 to 39, the needle shell has a needle outlet end from which the needle head is moved out of the needle shell for tattooing. The needle shell includes an abutting portion 10 disposed at the needle outlet end. When the needle head is extended, the tip end of the needle head passes through the abutting portion to be exposed out of the needle shell. When the needle head is retracted, the needle head is received in the abutting portion.

When the needle head is extended, a bottom surface of the needle body (for example, an end surface of the liquid guiding member that is connected to the substrate of the needle piercing portion) is exposed out of an end surface of the abutting portion.

The abutting portion defines a needle abutting channel 11. When the needle head is extended and when the needle head is subjected to the transverse force, a lower portion of a side wall of the needle body (a portion that is located near the needle piercing portion) abuts against an inner wall of the abutting portion, i.e., a channel wall of the needle abutting channel 11. The channel wall of the needle abutting channel 11 restricts radial oscillation of the needle body and the needle head. Specifically, the needle body, which may be the liquid guiding member as described in the above embodiments, includes a connection portion and an extending portion, the connection portion is located at an end of the extending portion, the connection portion is connected to the substrate. It is the connection portion that receives the substrate of the needle head and abuts against the channel wall of the needle abutting channel.

In the present embodiment, the needle shell is arranged with the abutting portion, and since the abutting portion defines the needle abutting channel 11. Firstly, when the needle head is retracted, the needle head is retracted and received in the needle abutting channel of the abutting portion. In this way, the free end of the needle head is not exposed out of the needle shell, such that the needle head is prevented from being worn out or broken when not in use, and the needle head can be normally used if required. In addition, during tattooing, the introduction needle may be moved to a proper location to generate the tattoo pattern, and in this case, the needle head needs to be retracted. By arranging the abutting portion and the needle abutting channel 11, when the introduction needle is moved to a proper location during tattooing, the needle head can be retracted and may not break the skin. When the needle head is extended out of the needle shell to break the skin transversely, the needle head is subjected to the transverse resistance. If the needle head takes only rigidity of the needle head itself to encounter the resistance to break the skin transversely, transversely may be easily bent or broken, causing damage to the user. Therefore, by arranging the abutting portion and defining the needle abutting channel, when the needle head is breaking the skin transversely, the channel wall of the needle abutting channel abuts against the needle body, and that is, the channel wall of the needle abutting channel provides support for the needle body to encounter the resistance for breaking the skin. In this way, the needle body is prevented from being bent or broken, ensuring stability of performing tattooing, an effect of the tattooing, and safety of the tattooing.

Figure 30:
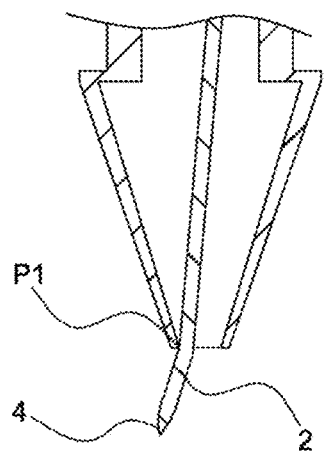
FIG. 30 is a structural schematic view of an introduction needle in the art being deformed when receiving a transverse force.

As shown in FIG. 30, in the art, a conventional introduction needle is used for tattooing. In this case, the tip end of the needle head is injected into the skin. When the needle head is breaking the skin transversely, there is no abutting portion at the needle output end of the needle shell. Therefore, no support is provided for the needle body that extends out of the needle shell. An abutting point P1 is the only point to abut against the needle body. Therefore, the transverse resistance and abutting point cooperatively form leverage principle of force, in which a smaller resistance may cause the needle body to be bent, affecting normal operation of the introduction needle.

Figure 31:
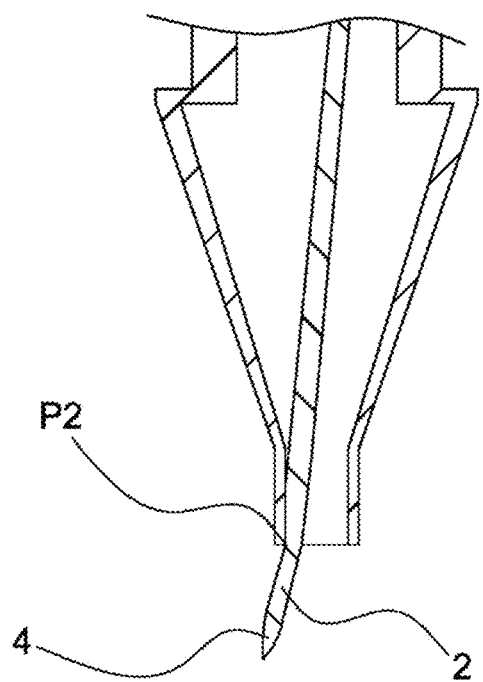
FIG. 31 is another structural schematic view of the introduction needle in the art being deformed when receiving the transverse force.

As shown in FIG. 31, in the art, a conventional introduction needle is used for tattooing, and in this case, a distance between the needle body and the channel wall of the needle abutting channel is not limited. That is, a diameter of the needle abutting channel is much larger than a diameter of the needle body. In this case, when the needle head is breaking the skin transversely, the needle body oscillates to a large extent within the needle abutting channel, such that a larger inertia and a large impact force are generated. The abutting portion takes only a small contact area P2 to abut against the needle body. The needle body takes the rigidity thereof to abut against an inner wall of a needle output port located at the end of needle shell. In this case, the needle body may be bent easily, affecting the normal operation of the introduction needle.

Figure 39:
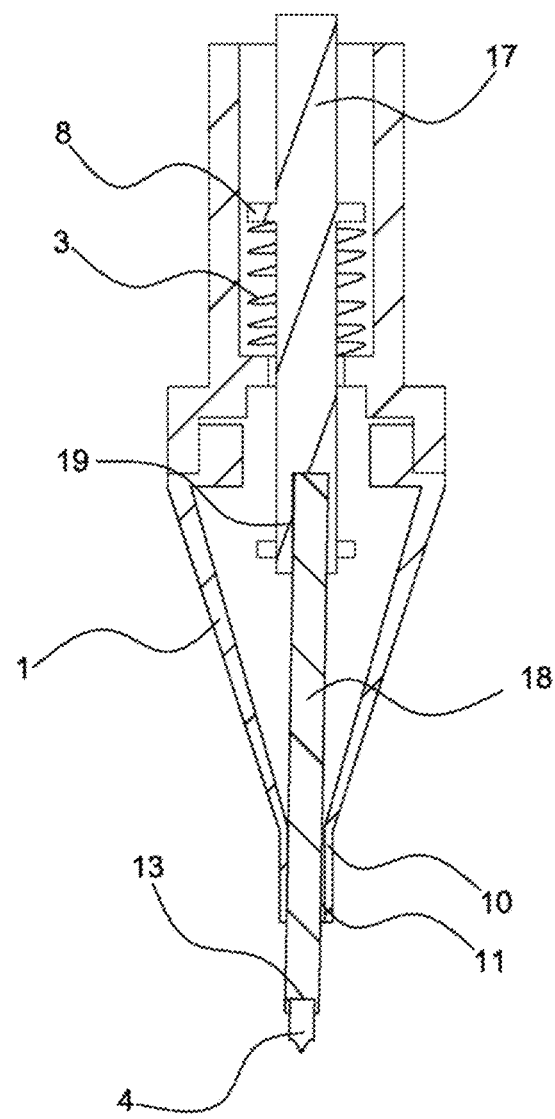
FIG. 39 is a structural schematic view of the introduction needle of FIG. 38, which is moved out of a needle shell and abuts against the needle shell when transversely breaking the skin, according to an embodiment of the present disclosure.

Therefore, in order to prevent the above two situations, in the present disclosure, the abutting portion is arranged. Furthermore, for most of the tattooing operations, the needle piercing portion needs to pierces into the skin vertically (i.e., a direction in which the needle piercing portion pierces into the skin is perpendicular to an outer surface of the pierced skin). In order to guide the needle head to break the skin in the transverse direction more precisely, an outer diameter of the component near the needle head (such as the abutting portion) shall not be too large to block a view sight of the operator. Therefore, a wall thickness of the abutting portion does not exceed 0.5 mm, such that the wall thickness may not affect the view sight of the operator. Since the wall thickness is not excessively thick, rigidity of the needle body to encounter deformation (such as bending) cannot be achieved based on the thickness of the abutting portion, and therefore, various components need to be arranged to cooperatively prevent the needle body from being deformed. In the present disclosure, a length of the abutting portion is greater than the outer diameter of the abutting portion. In this way, when the needle head is breaking the skin transversely and receives the resistance, the contact area between the needle body and the channel wall of the needle abutting channel is increased, such that the force applied to the abutting portion is dispersed. The abutting portion has a larger area, instead of a single point, to receive the resistance, and therefore, the needle head is prevented from being bent. In addition, the distance between the needle body and the channel wall of the needle abutting channel shall not be excessively large, such that the needle body is prevented from abutting against the channel wall at the single point. Therefore, the outer diameter of the needle body is smaller than an inner diameter of the needle abutting channel, such that the ink in the needle body can be normally and smoothly applied to the skin. Furthermore, the distance between the outer wall of the needle body and the channel wall of the needle abutting channel is smaller than a radius of the needle body. In this way, the needle body is prevented from oscillating significantly in the needle abutting channel, and therefore, the inertial impact may not be generated. The contact area, a contact length, and a contact range between the needle body and the needle abutting channel are increased. In this way, bending of the needle body is reduced, and the needle body is prevented from being deformed when breaking the skin transversely, ensuring the tattooing effect and the stability of the tattooing. As shown in FIG. 39, when the needle head is breaking the skin transversely, the needle body abuts against the channel wall of the needle abutting channel properly.

Figure 32:
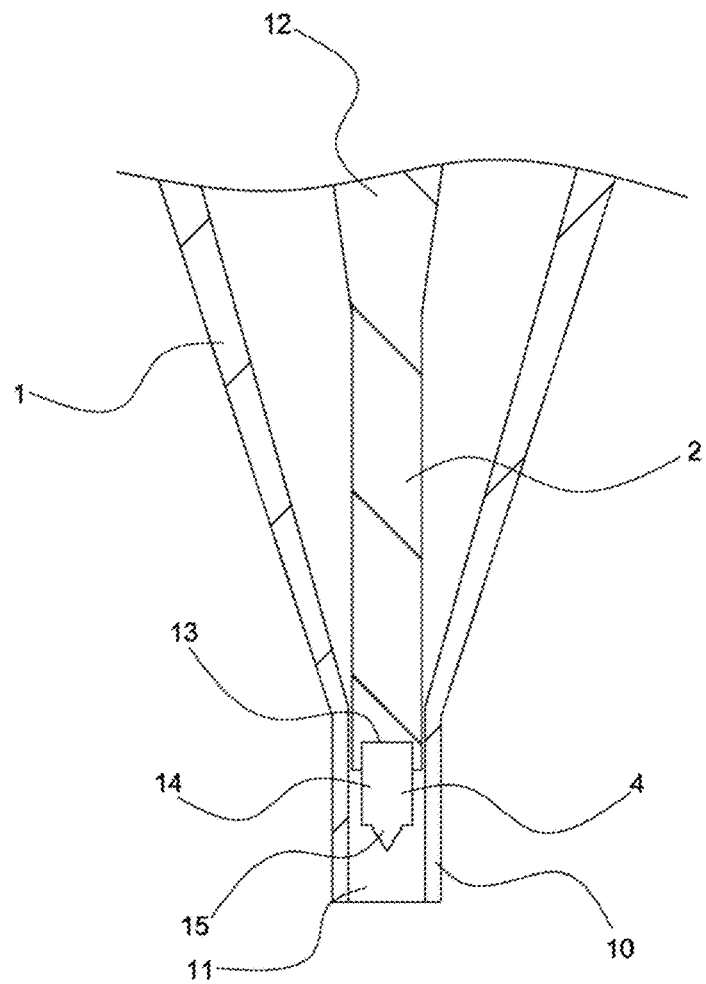
FIG. 32 is a cross-sectional view of an introduction needle according to an embodiment of the present disclosure.

As shown in FIG. 32, in another embodiment, an outer diameter of an upper portion of the needle body is larger than an outer diameter of a lower portion of the needle body. The upper portion of the needle body is connected to the lower portion of the needle body through a conical structure 12, allowing the outer diameter of the needle body to be changed gradually. When the needle head is extended out of the needle shell, only the lower portion of the needle body, which is located below the conical structure is inserted into the needle abutting channel. By configuring the needle body to have multiple segments which have gradually-changed outer diameters, strength and rigidity of the needle body is further improved, and the needle body may encounter the deformation optimally.

As shown in FIG. 26, FIG. 29, FIG. 32, and FIGS. 35 to 29, the end portion of the needle body defines a mounting slot 13, i.e., the end surface of the needle body is recessed. A top of the needle head, i.e., a portion of the substrate away from the needle tooth and the tip end, is embedded and mounted in the mounting slot. The substrate is in a tight fit with an inner wall of the mounting slot.

In an embodiment, the needle body may not define the mounting slot, and a surface of the substrate of the needle head away from the needle tooth is directly connected to the end surface of the needle body through an adhesive. The embedded mounting may enable the needle head to be connected with the needle body more firmly. In practice, the connection manner therebetween may be determined based on demands.

A gap is defined between the embedded portion of the needle head and a slot wall of the mounting slot, and the slot is configured to store the ink and serves as a liquid storage unit.

In the present embodiment, the introduction needle is a disposable product. The needle shell and the needle body may be made of plastics. Considering processing and precision, accuracy of dimension of the mounting slot may not be high, as long as the needle head can be tightly fitted with the mounting slot. However, when the needle head is tightly fitted with the mounting slot, a micro-gap may still be defined between the needle head and the slot wall of the mounting slot, and the micro-gap serves as the liquid storage unit that stores the ink for tattooing. Therefore, a temporary ink storage capacity is improved, enough coloring material may be provided while breaking the skin, ineffective tattoo operations, which injects no ink into the skin, may be reduced, and a color retention rate may be improved.

Figure 26:
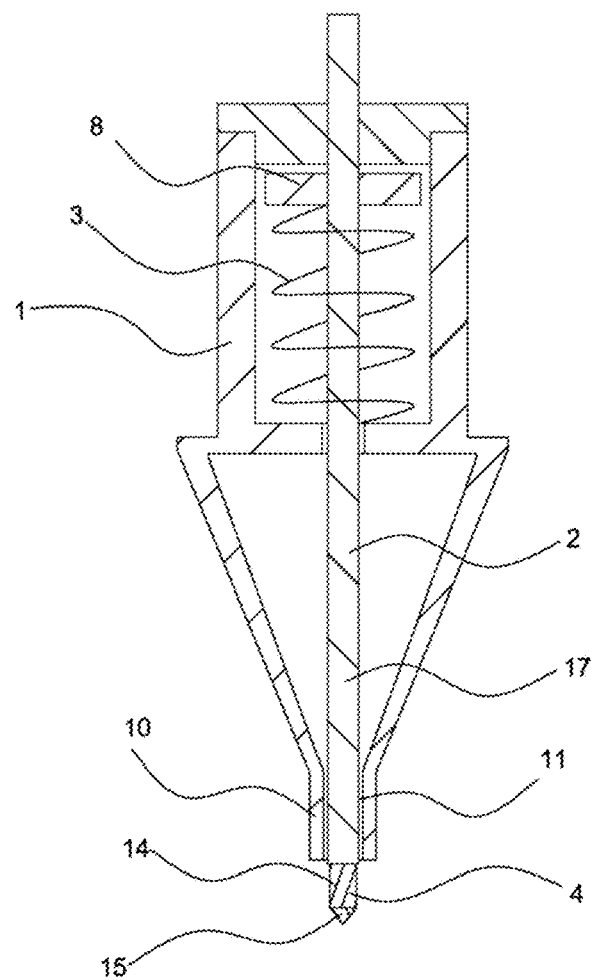
FIG. 26 is a structural schematic view of an introduction needle according to an embodiment of the present disclosure.

As shown in FIG. 26, FIG. 29, and FIGS. 32 to 29, the needle head includes a reinforcing portion 14 and a needle tooth 15, and the reinforcing portion 14 and the needle tooth 15 are configured as a one-piece structure. A non-tip end face of the needle tooth is connected to a first surface of the reinforcing portion, and a second surface of the reinforcing portion opposite to the first surface is connected to the end surface of the needle body. Specifically, the needle tooth 15 is the multifaceted structure having the sharp portion as described in the above, and the reinforcing portion 14 is the substrate connected to the needle tooth as described in the above.

The needle tooth has the tip end to break skin vertically. When the needle head is extended to break the skin transversely, the sharp portion of the needle head guides the needle head to move transversely and breaks the skin transversely. The reinforcing portion is configured to connect the needle head with the needle body. The reinforcing portion is directly embedded into the mounting slot at the end of the needle body. In this way, the needle head and the needle body may be connected to each other rapidly. Furthermore, the reinforcing portion allows the needle tooth to be connected to the needle body, enabling the needle tooth to be exposed out of the needle body to perform the tattooing.

In the present disclosure, the needle tooth is the multifaceted structure having 4 to 12 faces. The number of the faces is less than 12. This is because as the number of faces of the multifaceted structure increases, the multifaceted structure is configured to be more similar to a conical structure having a smooth and curved side face. As the number of faces of the multifaceted structure increases, the angle of the sharp portion may be increased, such that the sharp portion may be insufficiently sharp, affecting a skin-breaking effect, leading to a high resistance for breaking the skin. Therefore, the multifaceted structure having 4 to 12 faces is arranged herein. The angle of the sharp portion formed between every two adjacent faces is less than 150°, and a better skin-breaking effect is achieved. Of course, as the number of faces of the multifaceted structure decreases, the angle of the sharp portion is reduced. For example, when the multifaceted structure has 4 faces, the angle of the sharp portion is 90°. That is, as the angle of the sharp portion decreases, the sharp portion is sharper. As the number of faces of the multifaceted structure increases, the angle of the sharp portion is increased. In practice, the number of faces may be determined based on demands.

The reinforcing portion may be a cylindrical structure or a multifaceted structure. An area of the non-tip end face of the needle tooth is less than or equal to an area of the first surface of the reinforcing portion.

In the present disclosure, if the needle head is made of metal, the reinforcing portion may be cylindrical. If the needle head is made of a brittle material, such as ceramics, silicon, Plexiglas, and so on, the reinforcing portion may be configured as the multifaceted structure in order to perform production processes more conveniently and to increase a yield of the needle.

In an example, the reinforcing portion is the multifaceted structure. For example, the needle tooth is a multifaceted structure having six faces, and the reinforcing portion may be a multifaceted structure having six faces or four faces or eight faces. That is, the number of the faces of the multifaceted reinforcing portion does not have to be equal to the number of faces of the multifaceted needle tooth.

The non-tip end face of the needle tooth is connected to the first surface of the reinforcing portion and occupies a portion of the first surface of the reinforcing portion. The non-tip end face of the needle tooth is aligned with the rest portion of the first surface of the reinforcing portion. The non-tip end face of the needle tooth may be located inside edges of the first surface of the reinforcing portion.

Figure 33:
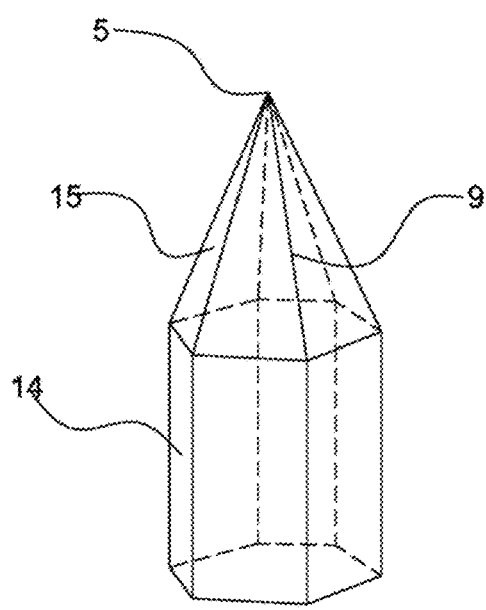
FIG. 33 is a perspective view of a needle piercing portion of the needle according to an embodiment of the present disclosure.
Figure 35:
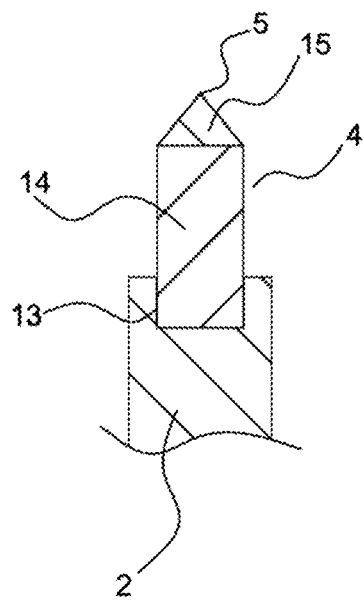
FIG. 35 is a cross-sectional view of the needle piercing portion shown in FIG. 33 being connected to a needle body according to an embodiment of the present disclosure.

As shown in FIGS. 33 and 35, in the present embodiment, the needle tooth is a multifaceted structure having six faces. The reinforcing portion is also multifaceted structure having six faces. An area of the non-tip end face of the needle tooth is equal to an area of the first surface of the reinforcing portion. Each face of the needle tooth has a bottom edge arranged on the first surface of reinforcing portion. An edge of each face on the first surface of the reinforcing portion is connected to a respective bottom edge of the needle tooth.

Figure 34:
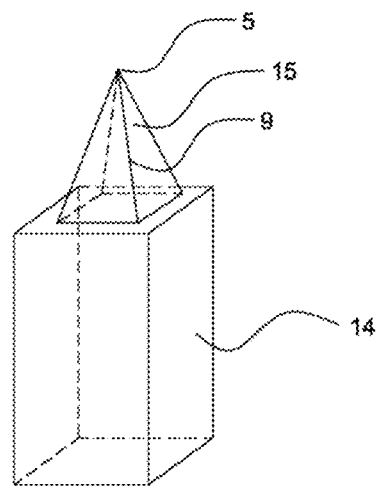
FIG. 34 is another perspective view of the needle piercing portion of the needle according to an embodiment of the present disclosure.
Figure 36:
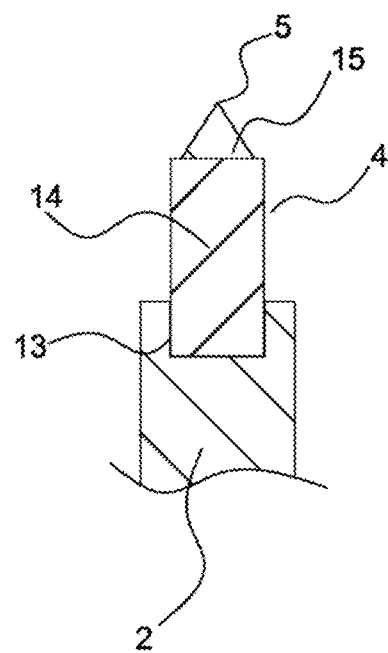
FIG. 36 is a cross-sectional view of the needle piercing portion shown in FIG. 34 being connected to the needle body according to an embodiment of the present disclosure.

As shown in FIGS. 34 and 36, in the present embodiment, the needle tooth is a multifaceted structure having four faces. The reinforcing portion is also multifaceted structure having four faces. The area of the non-tip end face of the needle tooth is less than the area of the first surface of the reinforcing portion. The non-tip end face of the needle tooth is located at a center of the first surface of the reinforcing portion.

Figure 37:
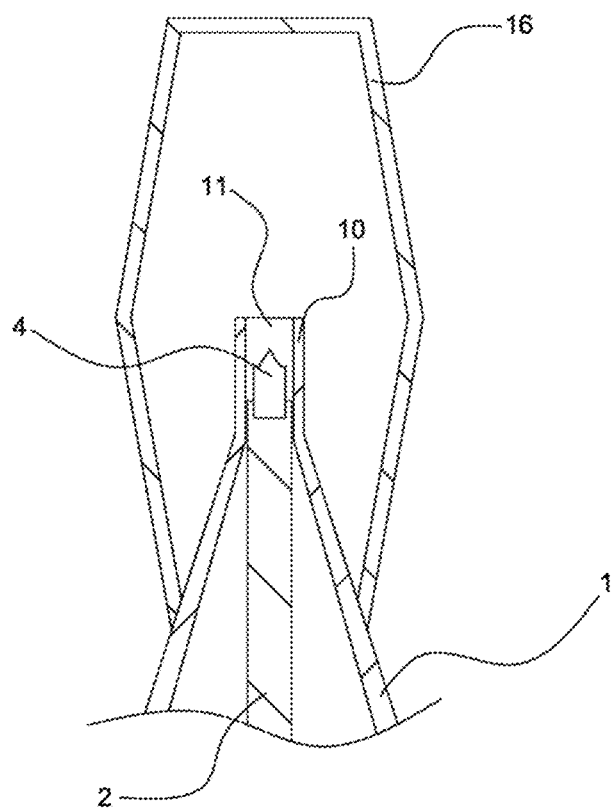
FIG. 37 is another structural schematic view of the introduction needle being connected to a protection cap according to an embodiment of the present disclosure.

As shown in FIG. 37, the needle output end of the needle shell is removably covered by a protective cap 16. A distance between an end face, which covers the needle output end, and an end surface of needle body is greater than a circumferential downwardly-moving distance of the needle head.

The protective cap prevents the introduction needle from hurting any person if the needle body and the needle head are mis-operated to be extended out of the needle shell. The distance between an end face, which covers the needle output end, and an end surface of needle body is greater than a maximum deformation length of the resilient member in the vertical direction. Therefore, when performing tattooing, if the protective cap is not removed by accident, the needle head may not collide with the protective cap, preventing the needle head from being damaged.

As shown in FIG. 26, in an embodiment, the needle body is a needle rod 17. The substrate of the needle head is connected to the bottom of the needle rod. In the present embodiment, the needle rod is a one-piece structure, the needle head is directly connected to the needle rod. The resilient member directly applies a restoring force to the needle rod toward a top of the rod (the top is a portion of the needle rod away from the tip end of the needle head). The top of the needle rod is contacted with the driving mechanism of the operation handle. The driving mechanism applies a force to the needle rod to push the needle rod to move downwardly. The driving mechanism and the resilient member drives the needle rod and the needle body to reciprocately move up and down to perform the tattooing.

In the present disclosure, the mounting slot is defined at the center of the bottom surface of the needle rod. During the tattooing, when the needle head is extended out of the needle shell, a lower portion of the needle rod abuts against the abutting portion of the needle shell. When the needle head is breaking the skin transversely, a side wall of the needle rod abuts against the channel wall of the needle abutting channel. In this case, the needle rod is the liquid guiding member as described in the above embodiments.

Figure 38:
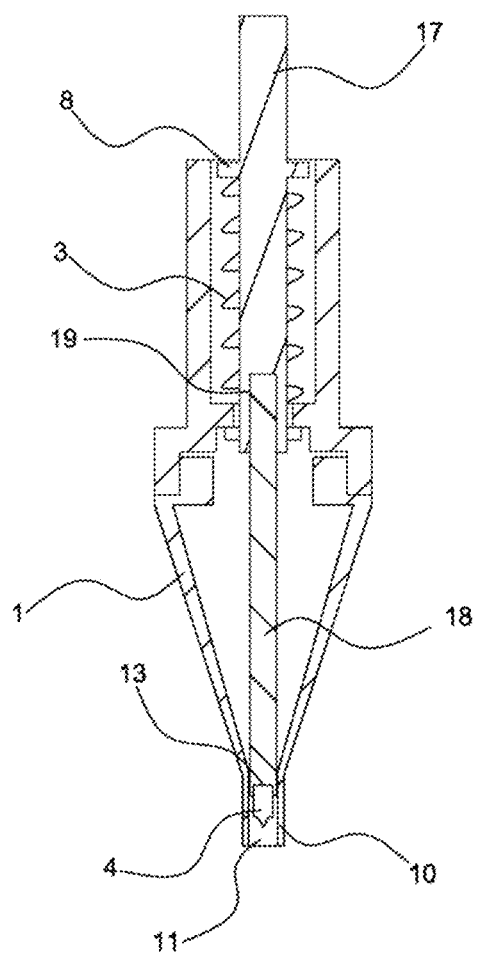
FIG. 38 is a structural schematic view of the introduction needle according to an embodiment of the present disclosure.

As shown in FIG. 38 and FIG. 39, in the present embodiment, the needle body comprises a needle rod 17 and a reinforcing rod 18. A bottom of the needle rod defines a mounting cavity 19. A top of the reinforcing rod is embedded and mounted in the mounting cavity. The top of the reinforcing rod is in tight fit with the mounting cavity. The substrate of the needle head is connected to the reinforcing rod. In the present embodiment, since an overall length of the needle body is relatively large, the needle rod 17 and the reinforcing rod 18 are manufactured separately and are connected to each other to form the needle body. In this way, difficulty of production is reduced, precision of production is reduced. In addition, the needle rod 17 and the reinforcing rod 18 are connected to each other by embedding, the connection may be performed conveniently and fast.

In the present embodiment, the mounting slot, in which the substrate of the needle head is embedded, is defined in an end surface of the reinforcing rod away from the needle rod 17. During the tattooing, when the needle head is extended out of the needle shell, the end surface of the reinforcing rod is exposed out of the abutting portion. When the needle head is breaking the skin transversely, a side wall of the reinforcing rod abuts against the channel wall of the needle abutting channel of the abutting portion.

The present disclosure further provides a tattoo needle as shown in FIG. 40 to FIG. 44.

The tattoo needle includes a needle portion 1 and a needle rod 2. The needle portion 1 has a tip end 3 to break the skin. A top of the needle portion 1 away from the tip end is connected to the needle rod 2.

An end of the needle rod 2 defines a mounting hole 4, mounting hole 4 and the needle rod 2 are coaxial with each other. The needle portion 1 includes a connection portion 5 and a needle tip portion 3. The connection portion 5 is a column structure having a plurality of faces connected to each other. The needle tip portion 3 is a multifaceted structure having a tip end 9 at a free end. A non-tip end face of the needle tip portion 3 is connected to a first surface of the connection portion 5.

To be noted that, the connection portion 5 may be the substrate in the above embodiments, and the needle tip portion 3 may be the needle tooth in the above embodiments.

An outer diameter of the connection portion 5 is smaller than an inner diameter of the mounting hole. The connection portion 5 is partially or entirely inserted in the mounting hole 4. An adhesive 6 is disposed between the connection portion 5 and the mounting hole 4. The connection portion 5 is connected to a slot wall of the mounting hole 4 by the adhesive 6.

For the needle tip portion 3, adjacent faces of the multifaceted structure are connected to each other to form a side prong 11. An angle between each side prong and the non-tip end face of the needle tip portion 3 is not greater than 90°. Alternatively, bottom edges of all of the plurality of faces cooperatively enclose a bottom surface of the needle tooth, and an angle between each coinciding side edge and the bottom surface of the needle tooth is less than or equal to 90 degrees.

The connection portion 5 is coaxially arranged with the mounting hole. Alternatively, an axis of the connection portion and an axis of the mounting hole are parallel to each other.

Figure 41:
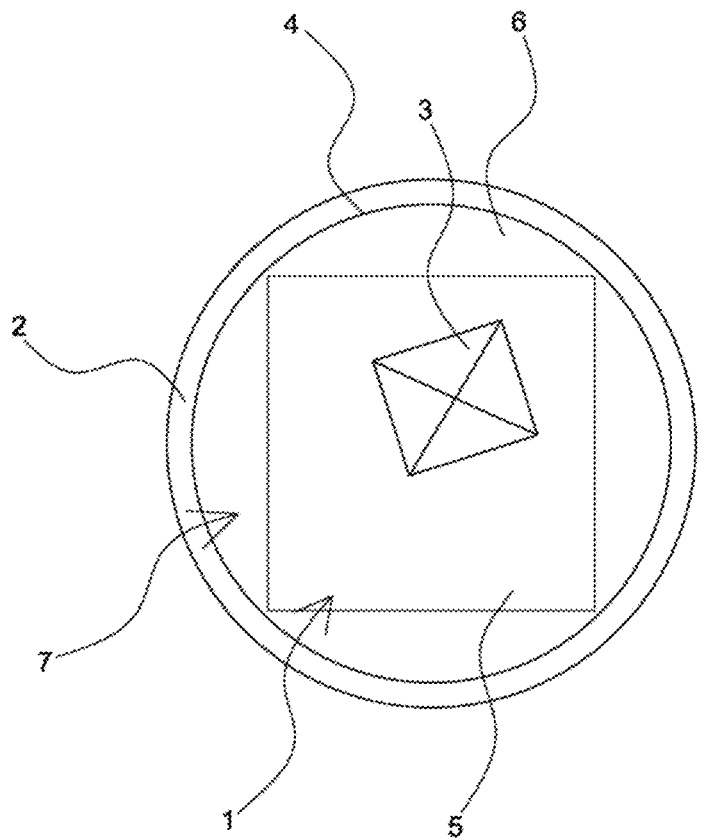
FIG. 41 is a bottom view of the introduction needle according to an embodiment of the present disclosure.
Figure 42:
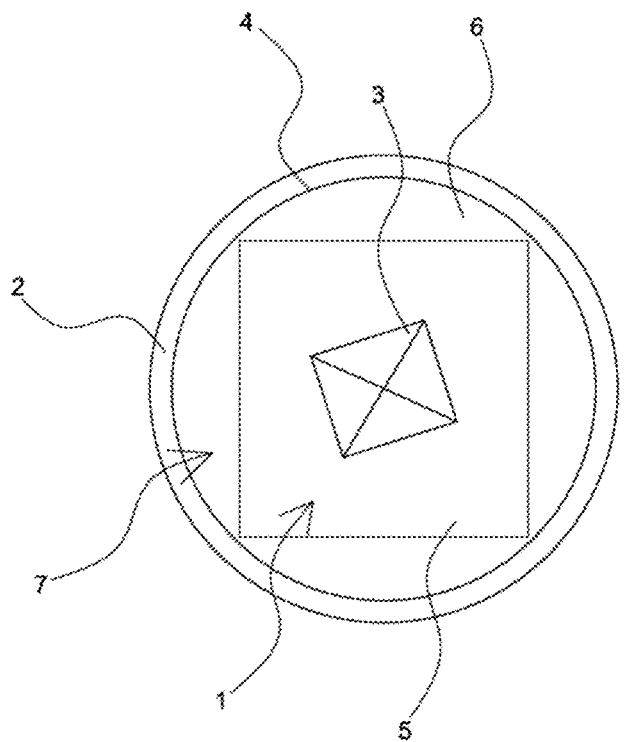
FIG. 42 is a bottom view of the introduction needle according to another embodiment of the present disclosure.
Figure 43:
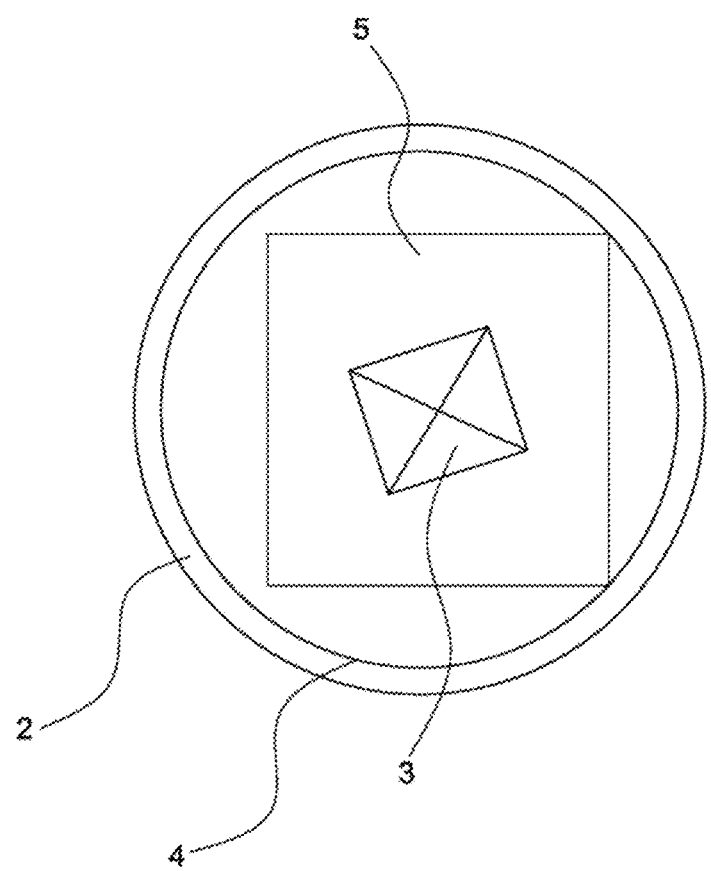
FIG. 43 is a bottom view of the introduction needle according to still another embodiment of the present disclosure.

In the present embodiment, when the connection portion is mounted to the mounting hole, the connection portion may be located at two types of locations. In one situation, the connection portion is located at a center of the mounting hole, and the connection portion does not contact the wall of the mounting hole. As shown in FIG. 41 and FIG. 42, the adhesive is filled between the outer wall of the connection portion and the wall of the mounting hole. In this case, the connection portion and the mounting hole are coaxial with each other, or the axis of the connection portion is close to the axis of the mounting hole, and the connection portion is almost coaxial with the needle rod. In another situation, the connection portion is biased towards a side of the mounting hole. A side of the connection portion is attached to the wall of the mounting hole, and a larger space is defined between the other side of the connection portion and the wall of the mounting hole. A significant spacing is defined between the axis of the connection portion and the axis of the mounting hole. The connection portion is not coaxial with the needle rod, as shown in FIG. 43.

As shown in FIG. 40 to FIG. 43, each side of the connection portion divides the mounting hole into a plurality of adhesive receiving units 7, and each adhesive receiving unit has an arc-shaped cross section. A curved edge of each adhesive receiving unit is a minor arc. Adjacent adhesive receiving units may be independent from each other. Alternatively, the adhesive receiving units are communicate with each other at ends of corresponding minor arcs. A cavity of the adhesive receiving unit is an interior of the minor arc.

In the present embodiment, the connection portion is a multifaceted column. When the connection portion is coaxial with the mounting hole, adjacent adhesive receiving units are communicated with each other at ends of corresponding minor arcs, as shown in FIG. 41 and FIG. 42. When the connection portion is non-coaxial with the mounting hole and at least one side of the connection portion is in contacted with the wall of the mounting hole, part of all adjacent adhesive receiving units can be independent from each other, and therefore, the cavity of the minor arc has a non-standard curved structure. The adhesive is received in the cavity of the minor arc and adheres the connection portion to the wall of the mounting hole of the needle rod. When the adhesive is being solidified, a slight vibration may be applied to a component that receives the adhesive to allow the adhesive to be uniformly distributed. In the present embodiment, the needle rod is slightly vibrated. The vibration is transmitted through the adhesive in the mounting hole, and the connection portion is also vibrated slightly. If the connection portion is cylindrical having a curved side face, the curved side face is smooth. When the adhesive is being solidified, the smooth curved side face may not generate enough friction, and therefore, the connection portion may rotate with respect to a longitudinal axis, affecting firmness of the solidification of the adhesive. However, in the present embodiment, the connection portion is a multifaceted column, and a plurality of prongs are formed by the plurality of faces on the side wall. Regardless of the connection portion contacting the wall of the mounting hole or not, when the connection portion rotates or tends to rotate with respect to the longitudinal axis, the prongs create a larger resistance to prevent the rotation of the connection portion. In this way, interference with the solidification process of the adhesive is reduced, and the connection portion may not fall off from the needle rod when the tattoo needle is in use.

Further, when the needle portion is assembled with the needle rod, the mounting hole needs to be placed to face upward, and the connection portion of the needle portion may be placed to face downward. In this way, when connection portion is mounted to the mounting hole, due to the minor arc, the adhesive flows along the wall of the mounting hole away from the interior of the mounting hole. In this way, even if excess adhesive is applied, the excess adhesive does not overflow to the side wall of the needle rod, and therefore, a diameter of the needle rod is not increased, the ink flowing down to the needle tooth is not affected, ensuring stability and precision of the tattooing.

In the present disclosure, a cross section of the mounting hole is circular, and a cross section of the connection portion is polygonal. In this way, when the connection portion is inserted into the cylindrical mounting hole, the mounting hole is not directional. The multifaceted column connection portion can be inserted into the mounting hole at an arbitrary angle, and no alignment is required, difficulty of assembling is reduced, the efficiency of assembling is improved, and the assembling is more convenient.

In the present disclosure, an angle between each prong and the non-tip end face of the of the needle tip portion is not more than 90°. In this way, the tip end of the of the needle tip portion may extend towards the axis of the of the needle tip portion and is prevented from deviating from the axis. The tip end may be a right angle or an acute angle, but cannot be an obtuse angle. This is because, during tattooing, the tip end needs to break the skin, and the right angle and the acute angle may break the skin easily and receives less resistance. If the tip end has the obtuse angle, the tip end is tilted outwardly, deviating away from the axis of the tip of the needle. In this case, the force applied to the needle tip portion is tilted when breaking the skin, the needle tip portion may be broken, causing safety issues. Furthermore, if the angle between the prong and the non-tip end face of the needle tip portion is the obtuse angle, when assembling the needle portion, the needle portion is clamped by a tool to be mounted to the needle rod; and after the assembling and when the clamping tool is to be removed from the needle portion, the tip end may be hooked with the clamping tool, and therefore, the assembling may not be performed easily.

Therefore, the needle tip portion is a multifaceted structure having the sharp portion, which may be easily processed and has better performance. In the present embodiment, the needle tip portion is a multifaceted structure having one tip end and four side faces. The angle between each prong and the non-tip end face of the needle tip portion is less than 90°. It is ensured that the tip end of the needle tip portion is sharp enough to perform the tattooing, and in addition, the prongs are tilted and sharp enough to break the skin transversely, ensuring quality and effect of the transverse breaking of the skin. Further, in the present disclosure, the connection portion is the multifaceted column, in which all prongs have an equal angle to each other. In the present embodiment, the connection portion has four faces and four prongs, and the four prongs have an equal angle to each other.

Figure 40:
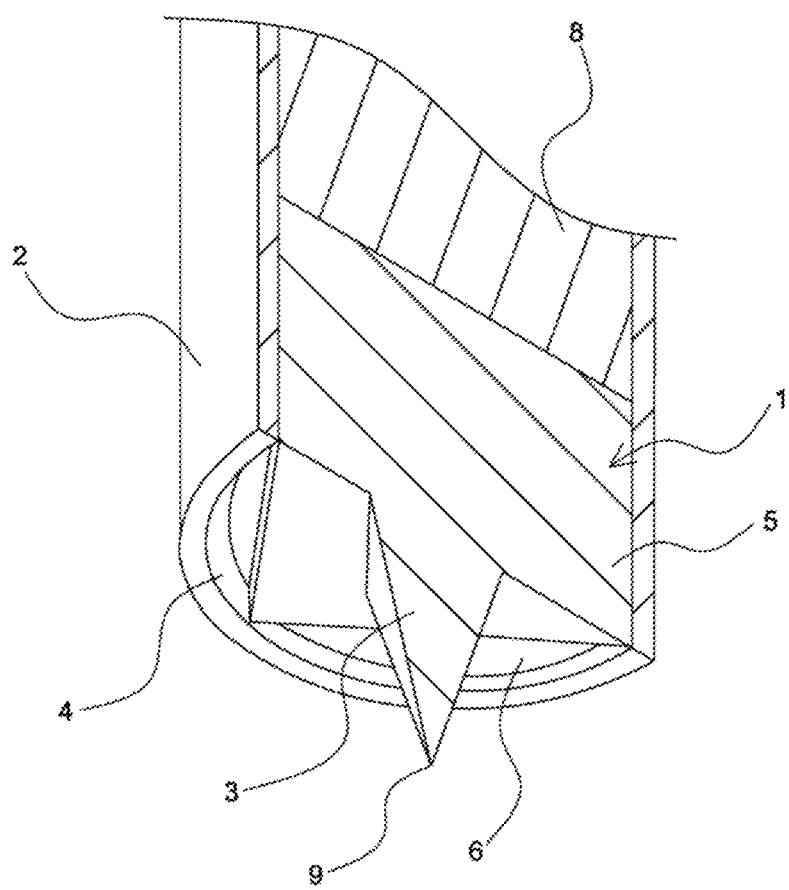
FIG. 40 is a cross-sectional view of a portion of an introduction needle according to an embodiment of the present disclosure.

As shown in FIG. 40, an angle of the tip end of a longitudinal cross section, taken along a plane that passes through the tip end of the needle tip portion, is not more than 90°. That is, the angle a2 is less than 90°. The angle of the tip is not the obtuse angle, ensuring sharpness of the tip end and facilitating to cut the skin.

The non-tip end face of the needle tip portion is fixedly connected to the first surface of the connection portion. Alternatively, the needle tip portion is integrally molded with the connection portion.

Figure 44:
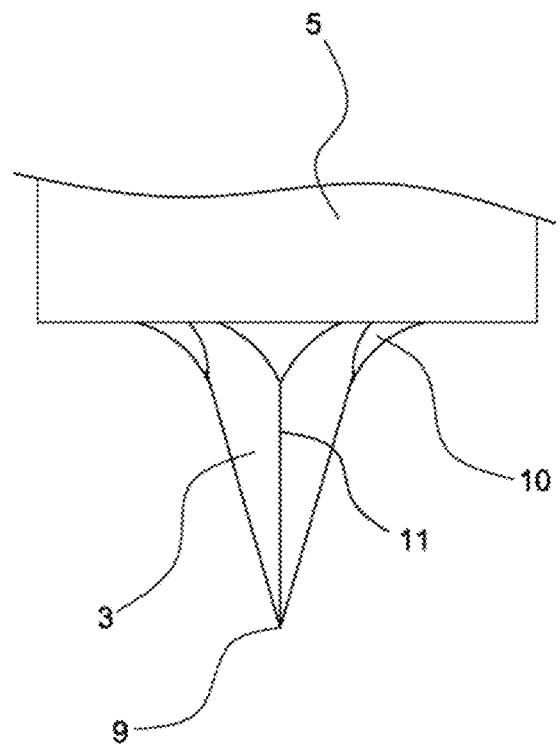
FIG. 44 is a side view of the needle piercing portion according to an embodiment of the present disclosure.

As shown in FIG. 44, the non-tip end face of the needle tip portion is connected to the first surface of the connection portion via a reinforcement member 10. The reinforcement member is connected to the prong of the needle tip portion (i.e., a connection where two adjacent faces of the needle tip portion are connected to each other). In the present embodiment, the reinforcement member has a curved reinforcement surface. The needle tip portion and the connection portion are configured as a one-piece structure. By arranging the curved reinforcement surface, the needle tip portion is connected to the connection portion through the curved surface. Especially when the needle tip portion is subjected to the transverse force, the connection between the needle tip portion and the connection portion receives a force in the radial direction. Therefore, by allowing the needle tip portion to be connected to the connection portion through the curved surface, the connection may not be cracked or broken, ensuring stability and safety of the tattooing.

As shown in FIG. 40, a positioning post 8 is arranged in the mounting hole to adjust an axial position of the needle portion and the needle rod. The positioning post 8 and the mounting hole are coaxial with each other. An outer diameter of the positioning post 8 is less than or equal to an inner diameter of the mounting hole. The positioning post 8 can move axially along the mounting hole to some extent, and the connection portion is disposed under the positioning post 8 (i.e., at an end of the positioning post 8 near the needle output end of the needle shell).

In the present disclosure, the positioning post is arranged at a proper position. A distance between an end surface of the positioning post and an end face of the mounting hole is adjusted (i.e., a length of the connection portion that can be mounted in the mounting hole is adjusted). Furthermore, the needle portion and the mounting hole are connected. In this way, needle portion having different lengths and needle tip portions having different protruding lengths may be applied, enhancing applicability of the introduction needle. According to different application scenarios, such as a scenario where a large transverse breaking force is to be applied, the length of the connection portion inserted in the mounting hole is longer. In this way, the needle tip portion may withstand a larger transverse breaking force and may not be detached from the needle rod, ensuring the stability and safety of the tattooing. In some cases, the needle tip portion needs to extend out of the needle shell longer, the distance between the end surface of the positioning post and the end face of the mounting hole is to be shortened. In this way, the distance between the tip end of the needle tip portion and the end face of the needle rod is longer. During tattooing, a larger length of the needle tip portion may extend out of the needle shell. In this way, the tattoo needle of the present disclosure may be applied broadly.

The second surface of the connection portion opposite to the first surface contacts the end surface of the positioning post. Alternatively, the second surface of the connection portion is adhered to the end surface of the positioning post.

As shown in FIG. 40, the second surface of the connection portion directly contacts the end surface of the positioning post.

As shown in FIG. 40, the firs surface of the connection portion is aligned with an end surface of the needle rod, alternatively, the firs surface of the connection portion is protruded out of the end surface of the needle rod.

In the present disclosure, the first surface of the connection portion is disposed out of the mounting hole but is protruded out of the needle rod.

In the present embodiment, the first surface of the connection portion is aligned with the end surface of the needle rod.

The area of the non-tip end face of the needle tip portion is less than or equal to the area of the first surface of the connection portion. Preferably, the area of the non-tip end face of the needle tip portion is less than the area of the first surface of the connection portion.

In the description of the present disclosure, the terms "an embodiment", "some embodiments", "examples", "specific examples", or "some examples" mean that specific features, structures, materials or characteristics described in one embodiment or one example are included in at least one embodiments or examples of the present disclosure. In the present specification, exemplary expressions of the above terms may not be directed to the same embodiment or the same example. Moreover, the specific features, structures, materials, or characteristics described may be combined in any one or more embodiments or examples in a suitable manner. In addition, any ordinary skilled person in the art may join and combine different embodiments or examples described in the present specification.

Although embodiments of the present disclosure have been shown and described above, it is to be understood that the above embodiments are exemplary and are not to be interpreted as a limitation of the present disclosure. Any ordinary skilled person in the art may perform changes, modifications and variations on the above embodiments within the scope of the present disclosure.

What is claimed is:

1. An introduction needle, comprising a needle piercing portion and a liquid guiding member, wherein the needle piercing portion comprises a needle tooth and a substrate; the needle tooth is fixedly disposed on a portion of a first side surface of the substrate; and
 when the needle tooth pierces into the skin, a remaining portion of the first side surface of the substrate is configured to abut against an outer surface of the skin;
 the liquid guiding member is configured to guide liquid to flow to the needle tooth;
 the liquid guiding member comprises a connection portion and an extending portion, the connection portion is located at an end of the extending portion;
 wherein an end face of the connection portion of the liquid guiding member away from the extending portion defines a receiving slot; and the substrate is at least partially received in the receiving slot.

2. The introduction needle according to claim 1, wherein a second side surface of the substrate opposite to the first side surface is received in the receiving slot, the first side surface is aligned with or protrudes from the end face of the connection portion of the liquid guiding member.

3. The introduction needle according to claim 2, further comprising a liquid storage unit for storing the liquid; wherein the liquid storage unit comprises a first liquid storage sub-unit and a second liquid storage sub-unit, the first liquid storage sub-unit is disposed in the extending portion of the liquid guiding member, the second liquid storage sub-unit is disposed between a portion of the substrate that is received in the receiving slot and a slot wall of the receiving slot; and
 the first liquid storage sub-unit, the second liquid storage sub-unit and the substrate are fluidly connected to each other to enable the liquid to flow from the first liquid storage sub-unit and the second liquid storage sub-unit to the substrate and the needle tooth.

4. The introduction needle according to claim 3, wherein, the first liquid storage sub-unit comprises a plurality of channels, the plurality of channels are disposed inside the liquid guiding member or defined on an outer wall of the liquid guiding member; and
 when at least one of the plurality of channels stores the liquid, the liquid is capable of being guided to flow along the at least one channel to the needle piercing portion.

5. The introduction needle according to claim 3, wherein the liquid guiding member comprises a plurality of liquid guiding sub-members, a gap is formed between every two adjacent sub-members of the plurality of liquid guiding sub-members, and the gap serves as the first fluid storage sub-unit.

6. A tattoo device, comprising the introduction needle according to claim 1 and a driving mechanism, wherein, the driving mechanism is configured to drive a liquid guiding member arranged in the introduction needle to move reciprocately to drive the needle piercing portion to inject into the skin and leave out of the skin repeatedly.

7. An introduction needle, comprising a needle piercing portion,
wherein the needle piercing portion comprises a needle tooth and a substrate; the needle tooth is fixedly disposed on a portion of a first side surface of the substrate;
when the needle tooth pierces into the skin, a remaining portion of the first side surface of the substrate is configured to abut against an outer surface of the skin to limit a depth of the needle tooth pierces into the skin;
the introduction needle further comprises a liquid guiding member configured to guide liquid to flow to the needle tooth, wherein the needle piercing portion is disposed at an end of the liquid guiding member, the substrate has a second side surface opposite to the first side surface, the second side surface is fixed to the end of the liquid guiding member, a central axis of the needle tooth is perpendicular to the first side surface of the substrate, and an extending direction of the liquid guiding member is substantially parallel to the central axis of the needle tooth;
the liquid guiding member comprises a connection portion and an extending portion, the connection portion is located at an end of the extending portion, the connection portion is connected to the substrate;
wherein the needle tooth comprises a plurality of faces and one tip end, the one tip end points away from the substrate.

8. The introduction needle according to claim 7, wherein each of the plurality of faces comprises one bottom edge and two side edges; the bottom edge is arranged on the substrate and the two side edges extend from two ends of the bottom edge in a direction away from the substrate; and
ends of the two side edges of all of the plurality of faces away from the substrate are connected to each other to form the one tip end.

9. The introduction needle according to claim 8, wherein adjacent side edges of two adjacent faces of the plurality of faces coincide with each other; and the coinciding side edge form a sharp portion.

10. The introduction needle according to claim 9, wherein, when the introduction needle pierces into the skin and moves in the skin transversely, the needle piercing portion is configured to adaptively rotate to enable the sharp portion to face a direction in which the needle piercing portion moves and breaks the skin.

11. The introduction needle according to claim 8, wherein bottom edges of all of the plurality of faces cooperatively enclose a bottom surface of the needle tooth, and an angle between each side edge and the bottom surface of the needle tooth is less than or equal to 90 degrees.

12. The introduction needle according to claim 11, wherein, the needle tooth has a cross section taken along a vertical plane perpendicular to the bottom surface of the needle tooth; and in the cross section, an interior angle of the one tip end is less than or equal to 90 degrees.

13. The introduction needle according to claim 8, further comprising a needle shell, wherein, the needle piercing portion and the liquid guiding member are arranged inside the needle shell and are rotatably and extendable-retractable with respect to the needle shell;
the needle shell has an opening, and the needle piercing portion is capable of at least partially protruding out of or being received into the needle shell through the opening.

14. The introduction needle according to claim 13, wherein, the needle shell comprises an abutting portion and a receiving portion; the abutting portion is located at an end of the receiving portion and defines an abutting channel and the opening; the opening is located at a free end of the abutting portion, the abutting channel and the opening are communicated with each other; and
when the needle tooth pierces into the skin and moves in the skin, the liquid guiding member abuts against a channel wall of the abutting channel and a wall of the opening.

15. The introduction needle according to claim 14, wherein, when the needle piercing portion is received in the needle shell, the needle piercing portion is received in the abutting channel of the abutting portion.

16. The introduction needle according to claim 15, wherein, a length of the abutting portion is greater than an outer diameter of the abutting portion.

17. The introduction needle according to claim 7, wherein, the number of the plurality of faces is 4 to 12.

* * * * *